United States Patent
Io et al.

(10) Patent No.: US 9,573,866 B2
(45) Date of Patent: Feb. 21, 2017

(54) AROMATIC HYDROCARBON PRODUCTION APPARATUS

(71) Applicant: TOYO ENGINEERING CORPORATION, Tokyo (JP)

(72) Inventors: Shouta Io, Narashino (JP); Toshihiro Wakabayashi, Narashino (JP)

(73) Assignee: TOYO ENGINEERING CORPORATION, Tokyo (JP)

( * ) Notice: Subject to any disclaimer, the term of this patent is extended or adjusted under 35 U.S.C. 154(b) by 443 days.

(21) Appl. No.: 14/076,825

(22) Filed: Nov. 11, 2013

(65) Prior Publication Data

US 2014/0142364 A1 May 22, 2014

(30) Foreign Application Priority Data

Nov. 16, 2012 (JP) .................................. 2012-251952

(51) Int. Cl.
*B01D 3/14* (2006.01)
*C07C 7/00* (2006.01)
(Continued)

(52) U.S. Cl.
CPC ............... *C07C 7/005* (2013.01); *B01D 3/007* (2013.01); *B01D 3/14* (2013.01); *B01D 3/143* (2013.01);
(Continued)

(58) Field of Classification Search
None
See application file for complete search history.

(56) References Cited

U.S. PATENT DOCUMENTS

| 4,041,091 A | 8/1977 | Henry |
| 5,783,047 A | 7/1998 | Aso et al. |

(Continued)

FOREIGN PATENT DOCUMENTS

| JP | 8-66601 A | 3/1996 |
| JP | 2004-16928 A | 1/2004 |

(Continued)

OTHER PUBLICATIONS

Superhidic: Energy Saving by Innovative Distillation System, Toyo Engineering Corporation, 2012 Japan-China-Korea Petroleum Technology Congress, Sep. 4, 2012.

(Continued)

*Primary Examiner* — Tam M Nguyen
(74) *Attorney, Agent, or Firm* — Knobbe Martens Olson & Bear LLP

(57) ABSTRACT

An apparatus includes a first distillation apparatus for obtaining a fraction enriched in C8+ aromatics; a second distillation apparatus for obtaining a fraction enriched in C8 aromatics; an adsorption separation apparatus for obtaining an extract containing para-xylene and a raffinate containing xylene isomers; a third distillation apparatus for obtaining a fraction enriched in para-xylene; and a fourth distillation apparatus for obtaining a fraction enriched in xylene isomers. The second distillation apparatus includes a high-pressure part including a rectifying section; a low-pressure part including a stripping section; a line for directing overhead vapor of the low-pressure part to a column bottom of the high-pressure part; a line for directing a column bottom liquid of the high-pressure part to a column top of the low-pressure part; and a heat exchange structure for transferring heat from the rectifying section to the stripping section.

12 Claims, 9 Drawing Sheets

(51) Int. Cl.
    *C10G 25/00*   (2006.01)
    *C10G 7/00*    (2006.01)
    *C10G 21/00*   (2006.01)
    *B01D 3/00*    (2006.01)

(52) U.S. Cl.
    CPC ............. *B01D 3/146* (2013.01); *C10G 7/00* (2013.01); *C10G 21/00* (2013.01); *C10G 25/00* (2013.01); *C10G 2300/1096* (2013.01)

(56) References Cited

U.S. PATENT DOCUMENTS

| | | |
|---|---|---|
| 2012/0048711 A1 | 3/2012 | Werba et al. |
| 2012/0048718 A1 | 3/2012 | Werba et al. |
| 2012/0048720 A1 | 3/2012 | Werba et al. |
| 2012/0085126 A1 | 4/2012 | Gupta et al. |
| 2012/0125761 A1 | 5/2012 | Nakaiwa et al. |
| 2013/0256115 A1 | 10/2013 | Wakabayashi et al. |

FOREIGN PATENT DOCUMENTS

| | | |
|---|---|---|
| JP | 2013-208561 A | 10/2013 |
| WO | 2009/017937 A2 | 2/2009 |
| WO | 2011/043199 A1 | 4/2011 |

OTHER PUBLICATIONS

Extended European Search Report issued Apr. 21, 2015 in EP Application No. 13190097.9.
Office Action issued Apr. 22, 2016 in CN Application No. 201310566301.6.

AROMATIC HYDROCARBON PRODUCTION APPARATUS

This application is based upon and claims the benefit of priority from Japanese patent application No. 2012-251952, filed on Nov. 16, 2012, the disclosure of which is incorporated herein in its entirety by reference.

BACKGROUND OF THE INVENTION

1. Field of the Invention

The present invention relates to an aromatic hydrocarbon production apparatus for obtaining aromatic hydrocarbons from a feedstock, such as reformate, containing aromatic hydrocarbons.

2. Description of the Related Art

Among aromatic hydrocarbons, benzene and xylene are significant basic chemicals used as raw materials for various industrial products. Benzene is mainly used for styrene monomer derivatives serving as raw materials for polystyrene or an ABS resin. Para-xylene, amongst xylenes, is used as a raw material for polyester fiber/resin and is one of basic chemicals in greatest demand.

An aromatic hydrocarbon production apparatus (also referred to as an aromatics complex) includes an aromatics extraction apparatus for separating benzene from a feedstock, such as reformate or pyrolysis gasoline, containing aromatic hydrocarbons and a para-xylene production apparatus for separating para-xylene from the feedstock. The aromatics complex is provided with a large number of distillation columns. Distillation is a unit operation that consumes large energy, and energy consumption is large in production of aromatic hydrocarbons.

In order to reduce the energy consumption, a multiple effect method is conventionally employed among distillation columns provided in an aromatics complex. Typically, an operation pressure of a xylene column, whose column bottom temperature is essentially so high that a heating furnace is necessary, is increased so that overhead vapor of the xylene column can be used as the heat source of a reboiler of another distillation column. Since energy necessary for the xylene column per se is essentially large, however, even if the energy is saved by using the overhead vapor of the xylene column as the heat source of a reboiler of another distillation column without reducing the energy necessary for the xylene column per se, there is a limit in reducing the energy consumption of the whole process.

In techniques described in US 2012/0048711A1 and US 2012/0048718A1, the energy is saved by using, as a xylene column, two distillation columns, that is, a low-pressure xylene column and a high-pressure xylene column. These literatures disclose a technique in which overhead vapor of the high-pressure xylene column is used as the heat source of a reboiler of the low-pressure xylene column and also as the heat source of a reboiler of another distillation column.

On the other hand, JP H08-66601A, JP 2004-16928A and International Publication No. WO2011/043199 disclose a heat integrated distillation column (hereinafter sometimes referred to as "HIDiC") capable of reducing energy consumption in distillation. In the HIDiC, heat is transferred by heat exchange from a rectifying section (a section located above a feedstock feed position) of a distillation column to a stripping section (a section located below the feedstock feed position), so as to reduce the amount of heat supplied to a reboiler and the amount of heat removed at a condenser, and thus, the thermal efficiency is improved.

SUMMARY OF THE INVENTION

An object of the present invention is to further reduce energy consumption in production of aromatic hydrocarbons.

According to various aspects of the present invention, an aromatic hydrocarbon production apparatus and a method for operating the same described below are provided.

1) An aromatic hydrocarbon production apparatus, including:

a first distillation apparatus configured to obtain, by distillation, from a feedstock, a fraction enriched in aromatic hydrocarbons having 8 or more carbon atoms and a fraction enriched in a component lighter than the aromatic hydrocarbons having 8 or more carbon atoms;

a second distillation apparatus configured to obtain, by distillation, from the fraction enriched in aromatic hydrocarbons having 8 or more carbon atoms obtained from the first distillation apparatus, a fraction enriched in aromatic hydrocarbons having 8 carbon atoms and a fraction enriched in an aromatic hydrocarbon having 9 or more carbon atoms;

an adsorption separation apparatus configured to separate para-xylene, by adsorption separation, from the fraction enriched in aromatic hydrocarbons having 8 carbon atoms obtained from the second distillation apparatus, and to obtain an extract and a raffinate, the extract being a stream containing a desorbent and para-xylene, and the raffinate being a stream containing the desorbent and a xylene isomer other than para-xylene;

a third distillation apparatus configured to obtain, by distillation, from the extract, a fraction enriched in para-xylene and a fraction enriched in the desorbent; and a fourth distillation apparatus configured to obtain, by distillation, from the raffinate, a fraction enriched in the xylene isomer other than para-xylene and a fraction enriched in the desorbent, wherein the second distillation apparatus is a distillation apparatus including:

a high-pressure part including the whole or a part of a rectifying section and configured to perform gas-liquid contact at a relatively high pressure;

a low-pressure part including the whole or a part of a stripping section and configured to perform gas-liquid contact at a relatively low pressure;

a line for directing an overhead vapor of the low-pressure part to a column bottom of the high-pressure part;

a line for directing a column bottom liquid of the high-pressure part to a column top of the low-pressure part; and a heat exchange structure configured to transfer heat from the rectifying section to the stripping section.

2) The apparatus according to 1), in which the first distillation apparatus includes a low-pressure distillation column operated at a relatively low pressure and a high-pressure distillation column operated at a relatively high pressure, which are arranged in series, the low-pressure distillation column of the first distillation apparatus is a distillation column configured to obtain, from the feedstock, the fraction enriched in aromatic hydrocarbons having 8 or more carbon atoms and the fraction enriched in a component lighter than the aromatic hydrocarbons having 8 or more carbon atoms, and the high-pressure distillation column of the first distillation apparatus is a distillation column configured to obtain, from the fraction enriched in a component lighter than the aromatic hydrocarbons having 8 or more carbon atoms obtained from the low-pressure distillation column of the first distillation apparatus, a fraction enriched in a hydrocarbon having from 6 to 7 carbon atoms and a fraction enriched in a component lighter than the hydrocarbon having from 6 to 7 carbon atoms.

3) The apparatus according to 2), in which the aromatic hydrocarbon production apparatus is configured to use an overhead vapor of the fourth distillation apparatus as a heat source of one or more reboilers selected from the group consisting of a reboiler provided for the low-pressure distillation column of the first distillation apparatus and a reboiler provided for the third distillation apparatus.

4) The apparatus according to 3), further including a fifth distillation apparatus configured to purify, by distillation, para-xylene contained in the fraction enriched in para-xylene obtained from the third distillation apparatus, wherein
the aromatic hydrocarbon production apparatus is configured to use the overhead vapor of the fourth distillation apparatus as a heat source of a reboiler provided for the fifth distillation apparatus.

5) The apparatus according to 3) or 4), in which the fourth distillation apparatus includes a low-pressure distillation column operated at a relatively low pressure and a high-pressure distillation column operated at a relatively high pressure, which are arranged in parallel,
the low-pressure distillation column of the fourth distillation apparatus is a distillation column configured to obtain, from a part of the raffinate, a fraction enriched in the xylene isomer other than para-xylene and a fraction enriched in the desorbent,
the high-pressure distillation column of the fourth distillation apparatus is a distillation column configured to obtain, from another part of the raffinate, a fraction enriched in the xylene isomer other than para-xylene and a fraction enriched in the desorbent, and
the overhead vapor of the fourth distillation apparatus is an overhead vapor of the high-pressure distillation column of the fourth distillation apparatus.

6) The apparatus according to 5), in which the aromatic hydrocarbon production apparatus is configured to use the overhead vapor of the high-pressure distillation column of the fourth distillation apparatus as a heat source of a reboiler provided for the low-pressure distillation column of the fourth distillation apparatus.

7) The apparatus according to 3) or 4), further including:
an aromatics extraction apparatus configured to obtain, by solvent extraction, from the fraction enriched in a hydrocarbon having from 6 to 7 carbon atoms obtained from the high-pressure distillation column of the first distillation apparatus, a stream enriched in an aromatic hydrocarbon having from 6 to 7 carbon atoms and a stream enriched in a non-aromatic hydrocarbon having from 6 to 7 carbon atoms;
a sixth distillation apparatus configured to obtain, by distillation, from the stream enriched in an aromatic hydrocarbon having from 6 to 7 carbon atoms obtained from the aromatics extraction apparatus, a fraction enriched in benzene and a fraction enriched in a component heavier than benzene; and
a seventh distillation apparatus configured to obtain, by distillation, from the fraction enriched in a component heavier than benzene obtained from the sixth distillation apparatus, a fraction enriched in toluene and a fraction enriched in a component heavier than toluene,
wherein the aromatic hydrocarbon production apparatus is configured to use the overhead vapor of the fourth distillation apparatus as a heat source of a reboiler provided for the seventh distillation apparatus.

8) The apparatus according to 7), in which the fourth distillation apparatus consists of a single distillation column, and the overhead vapor of the fourth distillation apparatus is an overhead vapor of this single distillation column.

9) The apparatus according to any of 1) to 8), in which an eighth distillation apparatus configured to remove, by distillation, an impurity contained in the raffinate is disposed between the adsorption separation apparatus and the fourth distillation apparatus.

10) A method for operating the aromatic hydrocarbon production apparatus according to 2), in which the method includes using an overhead vapor of the fourth distillation apparatus as a heat source of one or more reboilers selected from the group consisting of a reboiler provided for the low-pressure distillation column of the first distillation apparatus and a reboiler provided for the third distillation apparatus.

11) The method according to 10), in which the aromatic hydrocarbon production apparatus includes a fifth distillation apparatus configured to purify, by distillation, para-xylene contained in the fraction enriched in para-xylene obtained from the third distillation apparatus, and
the method includes using the overhead vapor of the fourth distillation apparatus as a heat source of a reboiler provided for the fifth distillation apparatus.

12) The method according to 10) or 11), in which the fourth distillation apparatus includes a low-pressure distillation column operated at a relatively low pressure and a high-pressure distillation column operated at a relatively high pressure, which are arranged in parallel,
the low-pressure distillation column of the fourth distillation apparatus is a distillation column configured to obtain, from a part of the raffinate, a fraction enriched in the xylene isomer other than para-xylene and a fraction enriched in the desorbent,
the high-pressure distillation column of the fourth distillation apparatus is a distillation column configured to obtain, from another part of the raffinate, a fraction enriched in the xylene isomer other than para-xylene and a fraction enriched in the desorbent, and
the method includes using an overhead vapor of the high-pressure distillation column of the fourth distillation apparatus as the overhead vapor of the fourth distillation apparatus.

13) The method according to 12), in which the method includes using the overhead vapor of the high-pressure distillation column of the fourth distillation apparatus as a heat source of a reboiler provided for the low-pressure distillation column of the fourth distillation apparatus.

14) The method according to 10) or 11), in which the aromatic hydrocarbon production apparatus further includes:
an aromatics extraction apparatus configured to obtain, by solvent extraction, from the fraction enriched in a hydrocarbon having from 6 to 7 carbon atoms obtained from the high-pressure distillation column of the first distillation apparatus, a stream enriched in an aromatic hydrocarbon having from 6 to 7 carbon atoms and a stream enriched in a non-aromatic hydrocarbon having from 6 to 7 carbon atoms;
a sixth distillation apparatus configured to obtain, by distillation, from the stream enriched in an aromatic hydrocarbon having from 6 to 7 carbon atoms obtained from the aromatics extraction apparatus, a fraction enriched in benzene and a fraction enriched in a component heavier than benzene; and a seventh distillation apparatus configured to obtain, by distillation, from the fraction enriched in a component heavier than benzene obtained from the sixth distillation apparatus, a fraction enriched in toluene and a fraction enriched in a component heavier than toluene, and the method includes using the overhead vapor of the fourth distillation apparatus as a heat source of a reboiler provided for the seventh distillation apparatus.

15) The method according to 14), in which the fourth distillation apparatus consists of a single distillation column, and the method includes using an overhead vapor of this single distillation column as the overhead vapor of the fourth distillation apparatus.

16) The method according to any of 10) to 15), in which the aromatic hydrocarbon production apparatus includes, between the adsorption separation apparatus and the fourth distillation apparatus, an eighth distillation apparatus configured to remove, by distillation, an impurity contained in the raffinate.

According to the present invention, the energy consumption in production of aromatic hydrocarbons can be further reduced.

DETAILED DESCRIPTION OF THE EXEMPLARY EMBODIMENT

Figure 1:
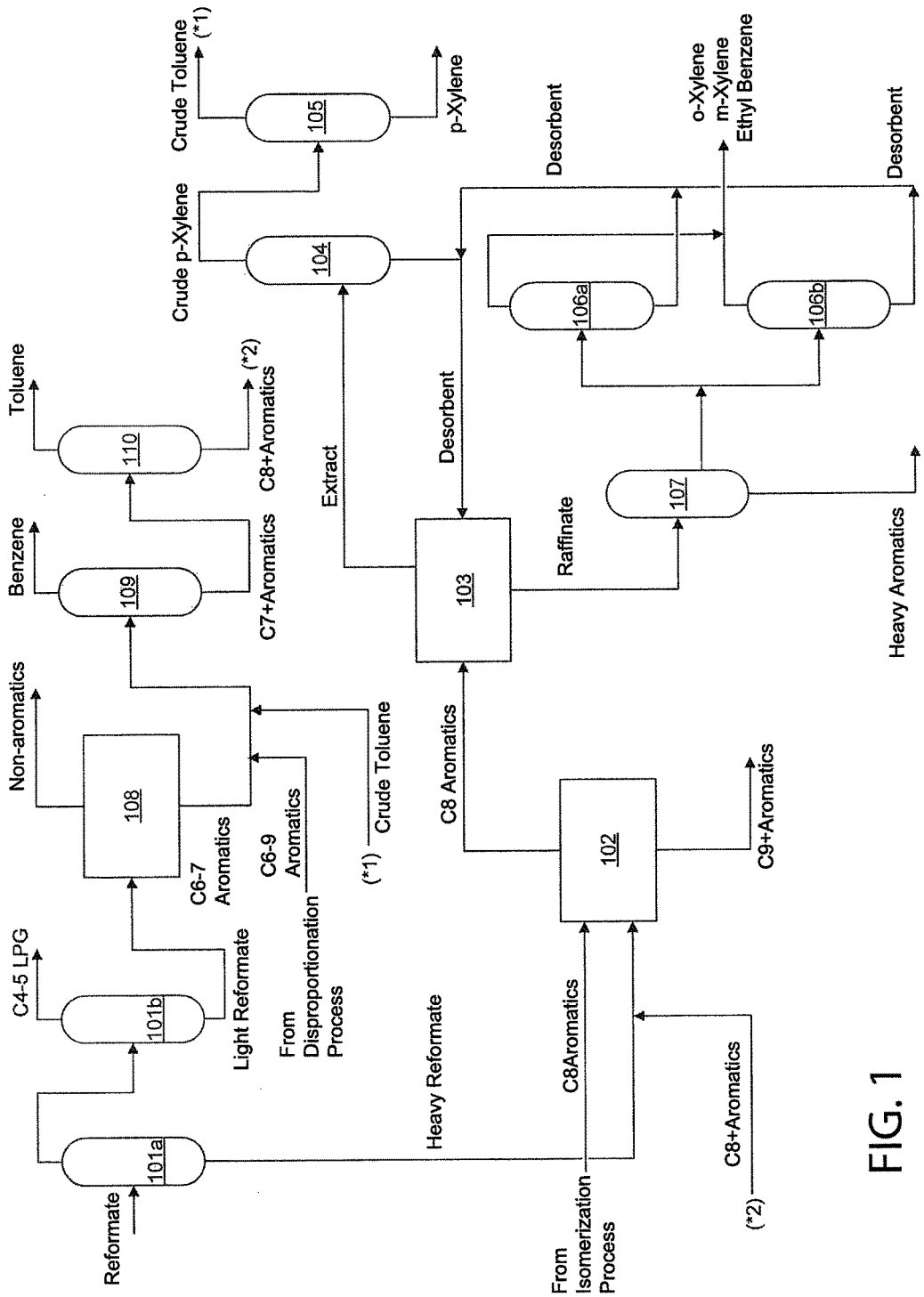
FIG. 1 is a schematic process flow diagram of an aromatic hydrocarbon production apparatus according to an embodiment of the present invention.

An aromatic hydrocarbon production apparatus according to the present invention is an apparatus for producing, from a feedstock, at least para-xylene and a xylene isomer(s) other than para-xylene (that is, one or more of ortho-xylene, meta-xylene and ethyl benzene). The aromatic hydrocarbon production apparatus may further produce benzene and toluene.

According to the present invention, since a HIDiC is employed as the second distillation apparatus (xylene column) and further the multiple effect method is employed, the energy consumption in the aromatic hydrocarbon production can be greatly reduced.

Hereinafter, a carbon number is sometimes expressed by using "C". For example, "C8" means "(having) 8 carbon atoms" and "C8+" means "(having) 8 or more carbon atoms". Furthermore, "aromatic hydrocarbon" is sometimes referred to as "aromatic". Besides, "A" used in a unit of a pressure means that the pressure is an absolute pressure.

The aromatic hydrocarbon production apparatus according to the present invention at least includes the first, second, third and fourth distillation apparatuses and an adsorption separation apparatus.

[First Distillation Apparatus]

The first distillation apparatus (sometimes referred to as a reformate splitter) is a distillation apparatus for obtaining, by distillation, from a feedstock, a fraction enriched in aromatic hydrocarbons having 8 or more carbon atoms (such as a heavy reformate described later; for example, containing 40 to 60% by mass of C8 aromatics) and a fraction enriched in a component(s) lighter than the aromatic hydrocarbons having 8 or more carbon atoms. The latter fraction is a stream containing, for example, a light reformate (for example, containing 60 to 70% by mass of C6 aromatics and C7 aromatics in total) and a liquefied petroleum gas (LPG) component(s) (for example, containing 90 to 99% by mass of C4 hydrocarbons and C5 hydrocarbons in total) described later. A stream of the light reformate and a stream of a component(s) lighter than the light reformate (a stream mainly composed of the liquefied petroleum gas component(s)) may be obtained separately.

The first distillation apparatus may include a low-pressure distillation column operated at a relatively low pressure (such as a low-pressure reformate splitter 101a shown in FIG. 1) and a high-pressure distillation column operated at a relatively high pressure (such as a high-pressure reformate splitter 101b shown in FIG. 1), which are serially arranged. Here, a "relatively low or high pressure" is based on comparison in the operation pressure between the low-pressure distillation column and the high-pressure distillation column of the first distillation apparatus. In other words, the low-pressure distillation column of the first distillation apparatus is operated at a lower pressure than the high-pressure distillation column of the first distillation apparatus.

The low-pressure distillation column of the first distillation apparatus is a distillation column for obtaining, from the feedstock, the fraction enriched in aromatic hydrocarbons having 8 or more carbon atoms (such as the heavy reformate described later: containing 40 to 60% by mass of C8 aromatics) and the fraction enriched in a component(s) lighter than the aromatic hydrocarbons having 8 or more carbon atoms (such as the stream containing the light reformate and the liquefied petroleum gas component(s) described later).

The high-pressure distillation column of the first distillation apparatus is a distillation column for obtaining, from the fraction enriched in a component(s) lighter than the aromatic hydrocarbons having 8 or more carbon atoms (such as the heavy reformate) obtained from the low-pressure distillation column of the first distillation apparatus, a fraction enriched in a hydrocarbon(s) having 6 to 7 carbon atoms (such as the light reformate described later; for example, containing 60 to 70% by mass of C6 aromatics and C7 aromatics in total) and a fraction enriched in a component(s) lighter than the hydrocarbon(s) having 6 to 7 carbon atoms (such as a light fraction mainly composed of the liquefied petroleum gas component(s) described later; for example, containing 90 to 99% by mass of C4 hydrocarbons and C5 hydrocarbons in total).

[Second Distillation Apparatus]

The second distillation apparatus is a HIDiC (such as HIDiC 102 shown in FIG. 1) for obtaining, by distillation, from the fraction enriched in aromatic hydrocarbons having 8 or more carbon atoms (for example, containing 40 to 60% by mass of C8 aromatics) obtained from the first distillation apparatus, a fraction enriched in aromatic hydrocarbons having 8 carbon atoms (for example, containing 95 to 99.9% by mass of C8 aromatics) and a fraction enriched in an aromatic hydrocarbon(s) having 9 or more carbon atoms (for example, containing 95 to 99.9% by mass of C9+ aromatics).

The fraction enriched in aromatic hydrocarbons having 8 or more carbon atoms obtained from the first distillation apparatus may be directly supplied to the HIDiC, but this fraction may be treated by another apparatus (for example, a clay treater described later) before being supplied to the HIDiC.

[Adsorption Separation Apparatus]

The adsorption separation apparatus (for example, an adsorption column 103 shown in FIG. 1) is an apparatus for separating para-xylene, by adsorption separation, from the fraction enriched in aromatic hydrocarbons having 8 carbon atoms obtained from the second distillation apparatus and obtaining an extract and a raffinate. The extract is a stream containing para-xylene and a desorbent. The raffinate is a stream containing a xylene isomer(s) other than para-xylene as well as the desorbent. In this apparatus, para-xylene is selectively adsorbed by an adsorbent, and the para-xylene is desorbed from the adsorbent by a desorbent, and thus para-xylene is separated from a xylene isomer(s) other than para-xylene.

[Third Distillation Apparatus (and Fifth Distillation Apparatus)]

The third distillation apparatus (such as an extract column 104 shown in FIG. 1) is a distillation apparatus for obtaining, by distillation, from the extract, a fraction enriched in para-xylene (for example, containing 95 to 99.9% by mass of para-xylene) and a fraction enriched in the desorbent (for example, containing 95 to 99.9% by mass of the desorbent). The third distillation apparatus may be configured with a single distillation column.

The aromatic hydrocarbon production apparatus may include a fifth distillation apparatus (such as a para-xylene purification column 105 shown in FIG. 1) for purifying, by distillation, the para-xylene contained in the fraction enriched in para-xylene obtained from the third distillation apparatus. The fifth distillation apparatus may be configured with a single distillation column.

From the fifth distillation apparatus, purified para-xylene can be obtained, and also a stream containing toluene can be obtained as a lighter fraction. This stream of the lighter fraction can be supplied, as crude toluene, to a sixth distillation apparatus (such as a benzene column 109 shown in FIG. 1) described later.

[Fourth Distillation Apparatus (and Eighth Distillation Apparatus)]

The fourth distillation apparatus is a distillation apparatus for obtaining, by distillation, from the raffinate, a fraction enriched in the xylene isomer(s) other than para-xylene (for example, containing 95 to 99.9% by mass of the xylene isomer(s) other than para-xylene) and a fraction enriched in the desorbent (for example, containing 95 to 99.9% by mass of the desorbent).

The fourth distillation apparatus may be configured with a single distillation column. Alternatively, the fourth distillation apparatus may include a low-pressure distillation column (such as a low-pressure raffinate column 106*a* shown in FIG. 1) operated at a relatively low pressure and a high-pressure distillation column (such as a high-pressure raffinate column 106*b* shown in FIG. 1) operated at a relatively high pressure, which are arranged in parallel.

Here, a "relatively low or high pressure" is based on the comparison in the operation pressure between the low-pressure distillation column and the high-pressure distillation column of the fourth distillation apparatus. In other words, the low-pressure distillation column of the fourth distillation apparatus is operated at a lower pressure than the high-pressure distillation column of the fourth distillation apparatus.

The low-pressure distillation column of the fourth distillation apparatus is a distillation column for obtaining, from a part of the raffinate, a fraction enriched in the xylene isomer(s) other than para-xylene and a fraction enriched in the desorbent.

The high-pressure distillation column of the fourth distillation apparatus is a distillation column for obtaining, from another part of the raffinate, a fraction enriched in the xylene isomer(s) other than para-xylene and a fraction enriched in the desorbent.

The raffinate obtained from the adsorption separation apparatus can be directly supplied to the fourth distillation apparatus, but the raffinate obtained from the adsorption separation apparatus may be treated by another apparatus before being supplied to the fourth distillation apparatus. For example, an eighth distillation apparatus (such as a pre-raffinate column 107 shown in FIG. 1) for removing, by distillation, an impurity(ies) (particularly, water and heavy aromatics formed by polymerization of the desorbent) contained in the raffinate may be provided between the adsorption separation apparatus and the fourth distillation apparatus, so that the raffinate obtained from the adsorption separation apparatus can be supplied to the fourth distillation apparatus after being subjected to a purification treatment in the eighth distillation apparatus. The eighth distillation apparatus may be configured with a single distillation column.

For example, the raffinate obtained from the adsorption separation apparatus may be divided into two streams, after being subjected to the purification treatment in the eighth distillation apparatus (namely, after an impurity(ies) is removed therefrom) as necessary. Then, one of the two streams may be supplied to the low-pressure distillation column of the fourth distillation apparatus and the other stream may be supplied to the high-pressure distillation column of the fourth distillation apparatus. Amounts of fluids to be distributed to the two streams can be adjusted by using a control valve as appropriate.

[Aromatics Extraction Apparatus]

An aromatics extraction apparatus (such as an aromatics extraction apparatus 108 shown in FIG. 1) is an apparatus for obtaining, by solvent extraction, from the fraction enriched in a hydrocarbon(s) having 6 to 7 carbon atoms obtained from the high-pressure distillation column of the first distillation apparatus, a stream enriched in an aromatic hydrocarbon(s) having 6 to 7 carbon atoms and a stream enriched in a non-aromatic hydrocarbon(s) having 6 to 7 carbon atoms. In this apparatus, an aromatic hydrocarbon(s) is separated from a non-aromatic hydrocarbon(s) by utilizing difference in solubility in a solvent.

[Sixth Distillation Column]

The sixth distillation column (such as the benzene column 109 shown in FIG. 1) is a distillation apparatus for obtaining, by distillation, from the stream enriched in an aromatic hydrocarbon(s) having from 6 to 7 carbon atoms obtained from the aromatics extraction apparatus, a fraction enriched in benzene and a fraction enriched in a component(s) heavier than benzene.

The sixth distillation apparatus may be configured with a single distillation column.

[Seventh Distillation Column]

A seventh distillation column (such as a toluene column 110 shown in FIG. 1) is a distillation apparatus for obtaining, by distillation, from the fraction enriched in a component(s) heavier than benzene obtained from the sixth distillation apparatus, a fraction enriched in toluene and a fraction enriched in a component(s) heavier than toluene. The fraction enriched in the component(s) heavier than toluene often contains an aromatic hydrocarbon(s) having 8 or more carbon atoms (C8+ aromatics), and this fraction may be supplied to the second distillation apparatus (such as the HIDiC 102 shown in FIG. 1). In this case, this fraction may be mixed with the fraction enriched in aromatic hydrocarbons having 8 or more carbon atoms (such as the heavy reformate) obtained from the first distillation apparatus before being supplied to the second distillation apparatus.

The seventh distillation apparatus may be configured with a single distillation column.

[Feedstock]

A feedstock contains at least the following components (here, an example of content of each component is described by way of "% by mass" based on the amount of the feedstock):
aromatic hydrocarbons having 8 carbon atoms (containing, for example, 3 to 10% by mass of para-xylene and 10 to 30% by mass of xylene isomer(s) other than para-xylene);
an aromatic hydrocarbon(s) having 9 or more carbon atoms (for example, 10 to 30% by mass (of, for example, cumene and normal propyl benzene)); and
a component(s) lighter than the aromatic hydrocarbons having 8 carbon atoms (for example, 3 to 15% by mass of benzene and 10 to 30% by mass of toluene as aromatic hydrocarbons having from 6 to 7 carbon atoms; 10 to 30% by mass of non-aromatic hydrocarbons having from 6 to 7 carbon atoms; and 1 to 5% by mass of hydrocarbons having from 4 to 5 carbon atoms as the component lighter than hydrocarbons having from 6 to 7 carbon atoms).

[Multiple Effect]

The aromatic hydrocarbon production apparatus is preferably configured so that the overhead vapor of the fourth distillation apparatus is used as the heat source of one or more reboilers selected from the group consisting of a reboiler provided for the low-pressure distillation column (for example, the low-pressure reformate splitter described later) of the first distillation apparatus and a reboiler provided for the third distillation apparatus (for example, the extract column described later).

In order to use the overhead vapor of the fourth distillation apparatus as the heat source of a reboiler of a certain distillation column or distillation apparatus (for example, an extract column), this reboiler (for example, the reboiler of the extract column) may be provided with a heat exchange structure for performing heat exchange between the overhead vapor of the fourth distillation apparatus and a column bottom fluid of this distillation column or distillation apparatus (for example, the extract column).

If the aromatic hydrocarbon production apparatus includes the fifth distillation apparatus (such as the para-xylene purification column described later), the aromatic hydrocarbon production apparatus may be configured so that the overhead vapor of the fourth distillation apparatus is used as a heat source of a reboiler provided for the fifth distillation apparatus.

Furthermore, if the fourth distillation apparatus includes the low-pressure distillation column and the high-pressure distillation column (such as the low-pressure raffinate column 106a and the high-pressure raffinate column 106b shown in FIG. 1) as described before, the overhead vapor of the high-pressure distillation column (for example, the high-pressure raffinate column 106b) of the fourth distillation apparatus may be used as the "overhead vapor of the fourth distillation apparatus" to be used as a heat source of a reboiler.

Moreover, if the fourth distillation apparatus includes the low-pressure distillation column and the high-pressure distillation column, the overhead vapor of the high-pressure distillation column (for example, the high-pressure raffinate column 106b) of the fourth distillation apparatus may be used as a heat source of a reboiler provided for the low-pressure distillation column (for example, the low-pressure raffinate column 106a) of the fourth distillation apparatus.

If the aromatic hydrocarbon production apparatus includes the aromatics extraction apparatus, the sixth distillation apparatus and the seventh distillation apparatus (such as the aromatics extraction apparatus 108, the benzene column 109 and the toluene column 110 shown in FIG. 1), the aromatic hydrocarbon production apparatus may be configured so that the overhead vapor of the fourth distillation apparatus is used as a heat source of a reboiler provided for the seventh distillation apparatus. In this case, it is preferred that the fourth distillation apparatus is configured with a single distillation column, and that the overhead vapor of this single distillation column is used as the "overhead vapor of the fourth distillation apparatus". However, even when the aromatic hydrocarbon production apparatus includes the aromatics extraction apparatus, the sixth distillation apparatus and the seventh distillation apparatus, the fourth distillation apparatus may include the low-pressure distillation column and the high-pressure distillation column as described above, and the overhead vapor of this high-pressure distillation column may be used as the "overhead vapor of the fourth distillation apparatus".

The aromatic hydrocarbon production apparatus is preferably configured to generate steam by using, as a heat source, an overhead vapor of a high-pressure part (such as a high-pressure xylene column of the HIDiC described later), and to use this steam as a heat source of one or more reboilers selected from the group consisting of a reboiler provided for the low-pressure distillation column (such as the low-pressure reformate splitter described later) of the first distillation apparatus, a reboiler provided for the high-pressure distillation column (such as the high-pressure reformate splitter described later) of the first distillation apparatus and a reboiler provided for the sixth distillation apparatus (such as the benzene column described later).

[Configuration of Aromatic Hydrocarbon Production Apparatus Described as Reference]

The present invention will now be described in detail with reference to the accompanying drawings, but it is noted that the present invention is not limited thereto.

First, for better understanding of the present invention, an example of a configuration of an aromatic hydrocarbon production apparatus for reference, not according to the present invention, namely, an aromatic hydrocarbon production apparatus in which a conventional distillation column (a single column) is applied to a xylene column, will be described with reference to FIG. 2.

Reformate produced by a reforming process of naphtha contains a large amount of aromatic hydrocarbons and is used as a raw material of aromatic hydrocarbons, particularly, a raw material of benzene and para-xylene. Other materials, such as a naphtha cracking residue (pyrolysis gasoline) obtained from a naphtha cracker, may be used as the raw material of aromatic hydrocarbons. A reformate is separated into a light reformate and a heavy reformate, the light reformate is used as a raw material in production of benzene and toluene, and the heavy reformate is used as a raw material in production of xylene.

Figure 2:
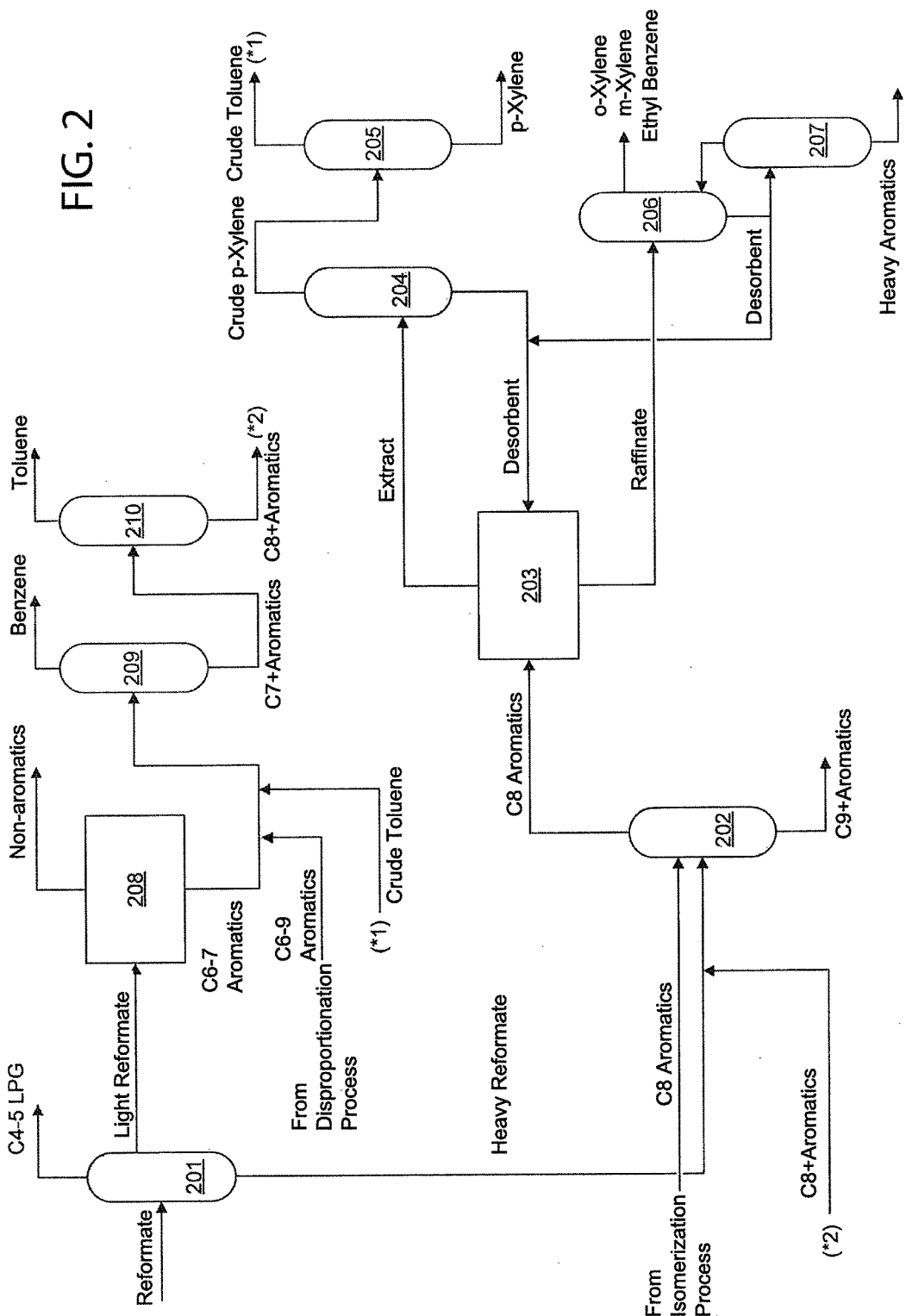
FIG. 2 is a schematic process flow diagram of an aromatic hydrocarbon production apparatus described as a reference.

As shown in FIG. 2, a reformate produced by the reforming process is separated by a splitter (a reformate splitter 201) into, for example, the following fractions:

a light fraction mainly composed of liquefied petroleum gas (LPG) components having from 4 to 5 carbon atoms (as a fraction enriched in components lighter than hydrocarbons having from 6 to 7 carbon atoms);

a light reformate mainly composed of hydrocarbons having from 6 to 7 carbon atoms (as a fraction enriched in hydrocarbons having from 6 to 7 carbon atoms); and a heavy reformate mainly composed of mixed xylene and aromatic hydrocarbons having 8 or more carbon atoms (C8+ aromatics) (as a fraction enriched in aromatic hydrocarbons having 8 or more carbon atoms).

The light reformate obtained as a side-cut product from the reformate splitter is fed to an aromatics extraction apparatus 208. The heavy reformate obtained from the column bottom is fed to a xylene column 202, after olefin components contained in the heavy reformate are treated by a clay treater (not shown), as appropriate.

The light reformate is separated into aromatic hydrocarbons and non-aromatic hydrocarbons by the aromatics extraction apparatus. The thus separated aromatics (mainly C6-7 aromatics) are fed to a benzene column 209, in which aromatic hydrocarbons having 7 or more carbon atoms are separated to produce benzene. In addition to the light reformate, a stream (flow) containing aromatic hydrocarbons having from 6 to 9 carbon atoms (C6-9 aromatics) fed from a disproportionation process may also be supplied to the benzene column 209. Further, a stream containing toluene (crude toluene) obtained from the column top of a para-xylene purification column may be supplied to the benzene column.

The aromatic hydrocarbons mainly having 7 or more carbon atoms separated by the benzene column 209 are fed to a toluene column 210 from the column bottom of the benzene column, so as to separate toluene and aromatic hydrocarbons having 8 or more carbon atoms. The separated toluene may be fed to the disproportionation process from the column top of the toluene column or may be withdrawn as a toluene product. The separated aromatic hydrocarbons having 8 or more carbon atoms are fed to the xylene column 202 from the column bottom of the toluene column.

From the column bottom of the xylene column to which the heavy reformate has been supplied, heavy aromatic hydrocarbons mainly composed of aromatic hydrocarbons having 9 or more carbon atoms (C9+ aromatics) are separated. Furthermore, the following streams may be fed to the xylene column: a stream from an isomerization process; a stream from a disproportionation process (In FIG. 2, the stream from a disproportionation process is fed to the xylene column after C6 aromatics and C7 aromatics are separated in the benzene column 209 and the toluene column 210, namely, fed to the xylene column as a part of a column bottom liquid of the toluene column 210. However, if a function to separate C6 aromatics and C7 aromatics is provided within the disproportionation process, a stream from the disproportionation process from which the C6 and C7 aromatics have been removed is fed to the xylene column directly, namely, without passing through the benzene column 209 and the toluene column 210); and a stream containing xylene (a column bottom liquid of the toluene column 210) separated after the aromatics extraction.

A stream separated in the xylene column from the heavy aromatic hydrocarbons and mainly composed of the aromatic hydrocarbons having 8 carbon atoms (C8 aromatics) is fed from the column top of the xylene column to an adsorption separation process. Specifically, a stream of aromatic hydrocarbons having 8 carbon atoms is fed to an adsorption column 203 in which para-xylene is separated, so as to obtain a stream mainly composed of para-xylene and a desorbent as an extract, and a stream mainly composed of xylene isomer(s) other than para-xylene (at least one of ortho-xylene, meta-xylene and ethyl benzene) and the desorbent as a raffinate. The adsorption separation process is a process based on the principle of elution chromatography, and in this process, while the aromatic hydrocarbons having 8 carbon atoms are moving through an adsorption layer, para-xylene having high affinity with an adsorbent is adsorbed onto the adsorbent so as to be separated from xylene isomer(s) other than para-xylene. The adsorbed para-xylene is desorbed from the adsorbent by a desorbent (such as para-diethyl benzene) and is withdrawn from the adsorption column. The extract is a stream essentially consisting of the desorbent and a component(s) having high adsorption power (mainly para-xylene) out of components supplied to the adsorption column. The raffinate is a stream essentially consisting of the desorbent and a component(s) having low adsorption power (mainly ortho-xylene, meta-xylene and/or ethyl benzene) out of the components supplied to the adsorption column.

The para-xylene withdrawn from the adsorption process together with the desorbent is fed to an extract column 204, in which para-xylene is separated from the desorbent. The separated desorbent is recycled to the adsorption column. The para-xylene from which the desorbent has been separated (crude para-xylene) is fed to a para-xylene purification column 205, in which a slight amount of a light component(s) (mainly toluene) is separated, so as to produce a para-xylene product. The slight amount of the light component(s) mainly composed of toluene (crude toluene) may be fed to the benzene column 209.

On the other hand, the xylene isomer(s) (at least one of ortho-xylene, meta-xylene and ethyl benzene) withdrawn from the adsorption column is fed, together with the desorbent, to a raffinate column 206, in which the xylene isomer(s) is separated from the desorbent. In the same manner as in the extract column, the desorbent separated in the raffinate column is recycled to the adsorption column. If the recycling of the desorbent is continued, heavy aromatic hydrocarbons may be formed by polymerization, and therefore, a part of the desorbent separated in the raffinate column is fed to a pre-raffinate column 207, in which heavy aromatic hydrocarbons (heavy aromatics) are removed. The desorbent from which the heavy aromatics have been removed is returned to the raffinate column. Furthermore, in order to compensate an amount of the desorbent decreased by the polymerization, a fresh desorbent may be supplied to the pre-raffinate column, so as to keep the amount of desorbent present in the system (not shown). From the column top of the raffinate column, a slight amount of water is separated (not shown). The xylene isomer(s) other than para-xylene obtained as a side fraction of the raffinate column may be fed to the isomerization process.

In the apparatus shown in FIG. 2, each of the reformate splitter 201, the xylene column 202, the extract column 204, the para-xylene purification column 205, the raffinate column 206, the pre-raffinate column 207, the benzene column 209 and the toluene column 210 is a distillation column (a single column) and includes a condenser at its column top and a reboiler at its column bottom.

Since a large number of distillation columns are provided in the aromatic hydrocarbon production apparatus as described above, it is desirable to reduce the energy consumption by employing the multiple effect method. In the aromatic hydrocarbon production apparatus described above as a reference, it is considered to be preferable that a heating furnace is used in the reboiler of the xylene column 202 which obtains a comparatively heavy fraction at its column bottom; the operation pressure of the xylene column is made higher; and the overhead vapor of the xylene column is used as the heat sources of the reboilers of the reformate splitter 201, the extract column 204 and the raffinate column 206. Furthermore, it is considered to be also preferable to make the operation pressure of the toluene column 210 higher, and to use the overhead vapor of the toluene column as the heat source of the reboiler of the benzene column 209.

[Configuration of the Aromatic Hydrocarbon Production Apparatus According to the Present Invention]

Next, the configuration of an aromatic hydrocarbon production apparatus according to an embodiment of the present invention will be described with reference to FIG. 1. The apparatus shown in FIG. 1 is different from the apparatus shown in FIG. 2, with regard to the schematic process flows shown in these drawings, in the configuration of the reformate splitter, the configuration of the xylene column, the configuration of the raffinate column and the arrangement of the raffinate column and the pre-raffinate column, and the rest is similar to each other. Needless to say, the apparatus shown in FIG. 1 may be different from the apparatus shown in FIG. 2 in a configuration not shown in these drawings, such as a configuration with regard to heat utilization, and in addition, in detail specifications of the respective units.

It should be noted here that the process flow shown in FIG. 2 does not accord with the present invention only because a HIDiC is not applied to the second distillation column, and that if the xylene column 202 of FIG. 2 is replaced with a HIDiC, the process flow of FIG. 2 can be regarded as an embodiment of the present invention.

Reformate Splitter

While a single column (specifically, the reformate splitter 201) is applied to a reformate splitter in the apparatus shown in FIG. 2, the apparatus of the present embodiment includes, as the splitter, low-pressure reformate splitter 101a and high-pressure reformate splitter 101b. The splitters 101a and 101b are arranged in series. The operation pressure of the low-pressure reformate splitter is lower than the operation pressure of the high-pressure reformate splitter. A feedstock (a reformate) is supplied to the low-pressure reformate splitter 101a, and a heavy reformate mainly composed of mixed xylene and aromatic hydrocarbons having 8 or more carbon atoms (C8+ aromatics) is obtained from the column bottom. A stream obtained from the column top (that is, a fraction enriched in components lighter than C8+ aromatics) is supplied to the high-pressure reformate splitter 101b. A light fraction mainly composed of liquefied petroleum gas (LPG) components having 4 to 5 carbon atoms is obtained from the column top of the high-pressure reformate splitter, and a light reformate mainly composed of hydrocarbons having from 6 to 7 carbon atoms is obtained from the column bottom.

Xylene Column

While a conventional distillation column (a single column) is applied to the xylene column 202 in the apparatus shown in FIG. 2, a HIDiC 102 is applied to the xylene column in the present invention.

The heavy reformate obtained from the column bottom of the low-pressure reformate splitter 101a is supplied to the HIDiC 102. Furthermore, a stream from an isomerization process, a stream from a disproportionation process and a stream containing xylene separated in an aromatics extraction process (that is, a column bottom liquid of the toluene column 110) may be fed to the HIDiC in the same manner as in the apparatus shown in FIG. 2. As a column bottom fluid of the HIDiC (more specifically, a column bottom fluid of a low-pressure xylene column described later), heavy aromatic hydrocarbons mainly composed of aromatic hydrocarbons having 9 or more carbon atoms (C9+ aromatics) are separated. As a column top fluid (more specifically, a column top fluid of a high-pressure xylene column described later), a stream mainly composed of aromatic hydrocarbons having 8 carbon atoms (C8 aromatics) resulting from the separation of the heavy aromatic hydrocarbons is obtained.

The HIDiC may be provided with the low-pressure xylene column and the high-pressure xylene column. The low-pressure xylene column is operated at a lower pressure than the high-pressure xylene column. Each of the low-pressure xylene column and the high-pressure xylene column is a single column (distillation column). These columns may be integrated with each other to form a single structure. The HIDiC may be further provided with a compressor, a condenser and a reboiler (HIDiC will be described in detail later). However, it is not always necessary to use two columns, and for example, a HIDiC including a double tube structure or a plate fin type heat exchanger may be employed.

Heat exchange is conducted between the high-pressure xylene column and the low-pressure xylene column (or heat exchange corresponding to such heat exchange is conducted). As a result, the heat duty of the reboiler(s) of the whole xylene column is drastically reduced. When the HIDiC is applied, the column bottom temperature of the xylene column (the column bottom temperature of the low-pressure xylene column) can be lowered, and there is no need to use a heating furnace as the heat source of the reboiler of the xylene column. Instead, high-pressure steam (having a saturation temperature of, for example, 250° C.) generally present in a petroleum refining plant or the like can be used as the heat source of the reboiler of the xylene column.

Configuration of Raffinate Column and Layout of Raffinate Column and Pre-Raffinate Column In the apparatus shown in FIG. 2, the raffinate obtained from the adsorption column 203 is supplied to the raffinate column (made of a single column) 206, and a part of a column bottom liquid of the raffinate column is supplied to the pre-raffinate column 207. In the apparatus according to the present embodiment, a raffinate obtained from the adsorption column 103 is directly fed to the pre-raffinate column 107, in which heavy aromatic hydrocarbons (that is, components generated by polymerization due to the recycling of the desorbent) are removed from the column bottom and a slight amount of water is removed from the column top (not shown), and a stream (mainly composed of the desorbent and xylene isomer(s) other than para-xylene) from which the heavy aromatic hydrocarbons and water have been thus removed is obtained as a side-cut.

This side-cut is supplied to the high-pressure raffinate column 106b. The desorbent is separated from the column bottom of the high-pressure raffinate column, and the xylene isomer(s) is obtained from the column top. The desorbent separated in the high-pressure raffinate column is returned to the adsorption column 103.

Depending upon heat balance achieved in the system, it is effective to provide a low-pressure raffinate column in order to reduce the energy consumption in the system. In this case, the side-cut separated from the pre-raffinate column is branched into two streams to be respectively supplied to the low-pressure raffinate column 106a and the high-pressure raffinate column 106b. In this case, the raffinate column includes two distillation columns arranged in parallel. In each of the low-pressure and high-pressure raffinate columns, the desorbent is separated from the column bottom and the xylene isomer(s) (at least one of ortho-xylene, meta-xylene and ethyl benzene) is obtained from the column top. The desorbents respectively separated in the low-pressure and high-pressure raffinate columns are both returned to the adsorption column 103. If there is the low-pressure raffinate column arranged in parallel to the high-pressure raffinate column, even when the heat balance within the system of the aromatic hydrocarbon production apparatus is changed (for example, when the composition of the feedstock is changed), the change can be coped with not by controlling the amount of overhead vapor by adjusting a reflux ratio of the high-pressure raffinate column but by controlling a distribution ratio between the flow rates of the fluids fed to the low-pressure raffinate column and the high-pressure raffinate column. Therefore, excessive heat duty of the heating furnace otherwise caused by increasing the reflux ratio can be avoided.

In the apparatus shown in FIG. 1, each of the low-pressure reformate splitter 101a, the high-pressure reformate splitter 101b, the extract column 104, the para-xylene purification column 105, the low-pressure raffinate column 106a, the high-pressure raffinate column 106b, the pre-raffinate column 107, the benzene column 109 and the toluene column 110 is a distillation column (a single column), and includes a condenser at its column top and a reboiler at its column bottom.

With Respect to Multiple Effect

In the aromatic hydrocarbon production apparatus shown in FIG. 2 as a reference, it is considered to be preferable to use the xylene column as the heat source of the multiple effect. If the HIDiC is applied to the xylene column, however, heat that can be taken out of the xylene column is smaller, and hence, it is preferred to rearrange the configuration for carrying out the multiple effect method. In the apparatus of the embodiment shown in FIG. 1, the following configuration is preferably employed for carrying out the multiple effect method.

With regard to the heat source used for the multiple effect, the operation pressure of the raffinate column is made higher (therefore, the operation temperature can be made higher), and the overhead vapor of the raffinate column is used as the heat source for the multiple effect. Depending upon the heat balance achieved within the system, the raffinate column may be divided into two columns (arranged in parallel), that is, the low-pressure raffinate column 106a and the high-pressure raffinate column 106b, and the operation pressure of the high-pressure raffinate column may be set at a relatively high pressure, and thus the high-pressure raffinate column can be used as the heat source for the multiple effect in the aromatic hydrocarbon production apparatus. The reboiler of the high-pressure raffinate column may be equipped with a heating furnace.

Specifically, the overhead vapor of the high-pressure raffinate column 106b may be used as at least one of the heat source of the reboiler of the low-pressure reformate splitter 101a and the heat source of the reboiler of the extract column 104. Also, the overhead vapor of the high-pressure raffinate column may be used as the heat source of the reboiler of the para-xylene purification column 105, and/or as the heat source of the reboiler of the low-pressure raffinate column 106a, and/or as the heat source of the reboiler of the toluene column 110. The overhead vapor of the high-pressure raffinate column may be used as all the five kinds of heat sources described above.

In order to use the overhead vapor of the high-pressure raffinate column as, for example, the heat source of the reboiler of the low-pressure raffinate column, a fluid can be withdrawn from the column bottom of the low-pressure raffinate column, and subjected to heat exchange with the overhead vapor of the high-pressure raffinate column by way of an appropriate heat exchange structure (a heat exchanger), and then the resulting fluid can be returned to the low-pressure raffinate column. In this manner, a part or the whole of heat input to the reboiler of the low-pressure raffinate column can be supplied from the overhead vapor of the high-pressure raffinate column.

According to the inventors' study, it has been found that, in the apparatus of the embodiment shown in FIG. 1, the overhead vapor of the high-pressure raffinate column can afford the whole heat input to the reboiler of the extract column 104, the whole heat input to the reboiler of the para-xylene purification column 105, the whole heat input to the reboiler of the low-pressure raffinate column 106a, the whole heat input to the reboiler of the toluene column 110 and a part of the heat input to the reboiler of the low-pressure reformate splitter 101a.

The rest of the heat input to the reboiler of the low-pressure reformate splitter 101a, the whole heat input to the reboiler of the high-pressure reformate splitter 101b and the whole heat input to the reboiler of the benzene column 109 can be supplied by medium-pressure steam (having a saturation temperature of, for example, 185° C.) generated in the xylene column 102, and steam (having a saturation temperature of, for example, 250° C.) generated by a separately provided boiler can be also used as the heat source. As the heat source of the reboiler of the pre-raffinate column 107, the column bottom fluid of the high-pressure raffinate column can be used.

Others

Thus, the column bottom temperature of the reformate splitter can be lowered by using two columns as the splitter. Also, the column bottom temperatures of the extract column and the low-pressure raffinate column can be relaxed by lowering their operation pressures. As a result, there is no need to increase the operation pressure of the high-pressure raffinate column (of which operation pressure may be, for example, 300 kPaA to 900 kPaA) as high as that of the conventional xylene column (operation pressure: 900 kPaA to 1,100 kPaA).

Conventionally, in order to reduce investment cost and plots, a reformate splitter is configured with a single column which separates hydrocarbons having 4 to 5 carbon atoms, a light reformate and a heavy reformate. When a single column is used, however, the operation pressure should be made higher for condensing the hydrocarbons having 4 to 5 carbon atoms with cooling water in the column top, and hence, the column bottom temperature tends to be higher. Therefore, the reformate splitter is preferably configured with two columns.

The reformate splitter (with an operation pressure of, for example, 300 kPaA to 400 kPaA) can be divided into two columns of a low-pressure reformate splitter (with an operation pressure of, for example, atmospheric pressure to 300 kPaA) and a high-pressure reformate splitter (with an operation pressure of, for example, 300 kPaA to 400 kPaA). The low-pressure reformate splitter separates a heavy reformate, and the high-pressure reformate splitter separates hydrocarbons having from 4 to 5 carbon atoms and a light reformate. By thus using two columns, the operation pressure of the low-pressure reformate splitter used for separating the heavy reformate can be lowered, and the column bottom temperature thereof can be lowered. Since the column bottom temperature can be thus lowered, when using (for the multiple effect) the overhead vapor of the high-pressure raffinate column as the heat source of the reboiler of the low-pressure reformate splitter, the column top temperature of the high-pressure raffinate column can be relaxed, so that the operation pressure of the high-pressure raffinate column can be lowered.

Moreover, in order to relax the column bottom temperature of the extract column, the operation pressure of the extract column may be set to 20 kPaA to 150 kPaA, and similarly, in order to relax the column bottom temperature of the low-pressure raffinate column, the operation pressure of the low-pressure raffinate column may be set to 20 kPaA to 150 kPaA.

Owing to the aforementioned configuration, the following advantages can be achieved:

1) The HIDiC is applied to the xylene column, the reformate splitter is configured with two columns, and further the multiple effect for enabling reduction of the whole energy consumption is reconstructed. Therefore, the energy consumption (in terms of primary energy) can be reduced by approximately 10% or more as compared with that in the apparatus as shown in FIG. 2.

2) In reconstructing the multiple effect for the whole apparatus, the operation pressure of the raffinate column is increased and the raffinate column is used as the heat source for the multiple effect. Depending upon the heat balance achieved within the system, a fluid to be supplied to the raffinate column may be divided and supplied to the high-pressure raffinate column and the low-pressure raffinate column, which are arranged in parallel; thus, the overhead vapor of the high-pressure raffinate column can be used (for the multiple effect) as the heat source of the reboiler of the low-pressure raffinate column or another distillation column.

3) Since the HIDiC is applied to the xylene column, the column bottom temperature of the xylene column (the column bottom temperature of the low-pressure xylene column) can be lowered, and therefore, there is no need to use a heating furnace as the heat source of the reboiler of the xylene column, but instead high-pressure steam can be used.

4) With respect to process stability (flexibility against load variation), when the low-pressure raffinate column is used, even if heat duty of a reboiler included in the aromatic hydrocarbon production apparatus is varied, the amount of energy exchange for the multiple effect can be adjusted by controlling the amounts of a fluid distributed to the low-pressure raffinate column and the high-pressure raffinate column without changing a reflux ratio of the raffinate column.

The disproportionation process is a process for producing benzene and xylene in great demand by disproportionation reaction for converting two molecules of toluene (C7 aromatic) into one molecule of benzene (C6 aromatic) and one molecule of xylene (C8 aromatic) and trans-alkylation reaction for reacting toluene (C7 aromatic) and trimethyl benzene (C9 aromatic) to produce two molecules of xylene (C8 aromatic).

The isomerization process is a process for producing para-xylene in great demand by converting the xylene isomer(s) other than para-xylene separated by the raffinate column into para-xylene.

[Basic Structure of HIDiC]

In the present invention, a high-pressure xylene column can be used as a high-pressure part (or a high-pressure column described with respect to examples of configurations of the HIDiC) described below, and a low-pressure xylene column can be used as a low-pressure part (or a low-pressure column described with reference to examples of configurations of the HIDiC) described below.

Components included in a HIDiC will be mentioned below.

A high-pressure part that includes the whole or a part of a rectifying section and performs gas-liquid contact at a relatively high pressure A low-pressure part that includes the whole or a part of a stripping section and performs gas-liquid contact at a relatively low pressure The terms of the "rectifying section" and the "stripping section" used regarding a distillation operation have been used for a long period of time with respect to a distillation apparatus, particularly a continuous distillation apparatus. The rectifying section corresponds to a section located above a feedstock feeding position in a conventional distillation column configured with a single column. The stripping section corresponds to a section located below the feedstock feeding position in the conventional distillation column. In other words, the rectifying section is a section of a distillation apparatus (typically, a distillation column) through which a fraction lighter than the feedstock flows. The stripping section is a section of a distillation apparatus (typically, a distillation column) through which a fraction heavier than the feedstock flows.

The operation pressure of the high-pressure part is set to be higher than the operation pressure of the low-pressure part so that the temperature of the rectifying section is higher than the temperature of the stripping section and thus heat can be transferred from the rectifying section to the stripping section by indirect heat exchange. Here, a "relatively high or low pressure" is based on comparison between the pressures of the low-pressure part and the high-pressure part with each other.

The high-pressure part basically corresponds to the rectifying section and the low-pressure part basically corresponds to the stripping section. Accordingly, in the most basic configuration of the HIDiC, the high-pressure part includes the rectifying section but does not include the stripping section, and the low-pressure part includes the stripping section but does not include the rectifying section. In other words, the high-pressure part includes the whole of the rectifying section and the low-pressure part includes the whole of the stripping section. However, a configuration of a HIDiC is not limited to such a configuration. The low-pressure part may include the whole of the stripping section and also a part of the rectifying section, while the rest of the rectifying section may be included in the high-pressure part. Alternatively, the high-pressure part may include the whole of the rectifying section and also a part of the stripping section, while the rest of the stripping section may be included in the low-pressure part.

In other words, the basic structure of the HIDiC is a structure that is obtained by dividing a conventional distillation column, using a feedstock feed position as a boundary, into two regions (a high-pressure part including the whole of the rectifying section, and a low-pressure part including the whole of the stripping section). The structure of the HIDiC is not, however, limited to this structure. It is also possible to employ a structure that is obtained by dividing a conventional distillation column into two regions at a position above the feedstock feed position, namely, a structure in which a single column is partitioned (a position located partway along the rectifying section is used as a boundary) into two regions (a low-pressure part including the whole of the stripping section and a part of the rectifying section, and a high-pressure part not including the stripping section but including the rest of the rectifying section). Alternatively, it is possible to employ a structure in which a conventional distillation column is partitioned, (a position located partway along the stripping section is used as a boundary) into two regions (a high-pressure part including the whole of the rectifying section and a part of the stripping section, and a low-pressure part not including the rectifying section but including the rest of the stripping section).

Naturally, if one of the high-pressure part and the low-pressure part includes both the rectifying section and the stripping section, the other never includes both of the rectifying section and the stripping section.

Each of the high-pressure part and the low-pressure part is typically formed by using a single column (vessel). A high-pressure column forming the high-pressure part and a low-pressure column forming the low-pressure part may be provided so as to be installed independently from each other. Alternatively, the high-pressure column and the low-pressure column may be integrated with each other to form a single structure. For example, it is possible to divide the inside of a single vessel by a partition wall (a member through which fluid cannot pass) for forming two regions, and to use one of the regions as the high-pressure column and the other as the low-pressure column.

A Line for Directing an Overhead Vapor of the Low-Pressure Part to the Column Bottom of the High-Pressure Part In a conventional distillation column, vapor ascends from a lower section (the stripping section) of the column to an upper section (the rectifying section). In the HIDiC, since the stripping section and the rectifying section are basically separated (partitioned), this line is provided for enabling such a stream of the vapor.

This line is provided with pressurizing means, such as a compressor, for transferring a vapor from the low-pressure part (having a relatively low pressure) to the high-pressure part (having a relatively high pressure).

A Line for Directing a Column Bottom Liquid of the High-Pressure Part to the Column Top of the Low-Pressure Part.

In a conventional distillation column, liquid descends from an upper section (the rectifying section) of the column to a lower section (the stripping section). In the HIDiC, since the stripping section and the rectifying section are basically separated (partitioned), this line is provided for enabling such a stream of the liquid. This stream is sometimes referred to as an "intermediate reflux", and this line is sometimes referred to as an "intermediate reflux line".

A Heat Exchange Structure for Transferring Heat from the Rectifying Section to the Stripping Section As described in JP H08-66601A or JP 2004-16928A, if the inside and the outside of a tube are used as the rectifying section (the high-pressure part) and the stripping section (the low-pressure part), the tube wall functions as a heat transfer surface. That is, a shell and tube type heat exchange structure can be employed.

In the HIDiC as described in WO 2011/043199, a heat exchange structure can include one of or both of the following a and b:

a) a heat exchanger provided in the rectifying section (typically, the rectifying section included in the high-pressure part), and a line for withdrawing a liquid from the stripping section (typically, the stripping section included in the low-pressure part) and passing the liquid through this heat exchanger, and returning the resulting fluid to this stripping section; and b) a heat exchanger provided in the stripping section (typically, the stripping section included in the low-pressure part), and a line for withdrawing a vapor from the rectifying section (typically, the rectifying section included in the high-pressure part), passing the vapor through this heat exchanger, and returning the resulting fluid to this rectifying section.

Alternatively, it is possible to employ a structure in which a heat exchanger is provided outside the high-pressure part and outside the low-pressure part (typically, outside the high-pressure column and outside the low-pressure column), a liquid is withdrawn from the stripping section (typically the stripping section included in the low-pressure part) and returned via this heat exchanger to this stripping section, and vapor is withdrawn from the rectifying section (typically, the rectifying section included in the high-pressure part) and returned via this heat exchanger to this rectifying section, thereby conducting heat exchange between these fluids.

The heat exchange structure may be any structure as long as heat can be transferred ultimately from the rectifying section to the stripping section, and the heat exchange structure can be realized without directly using any of a fluid present in the rectifying section and a fluid present in the stripping section. For example, a fluid discharged from the rectifying section and having a relatively high pressure (high temperature) can be used in place of a fluid present in the rectifying section. Besides, a fluid which is to be fed into the stripping section and has a relatively low pressure (low temperature) can be used in place of a fluid present in the stripping section. For example, by exchanging heat between a feedstock which is to be fed into the stripping section (typically, the stripping section included in the low-pressure part) and the overhead vapor withdrawn from the column top of the rectifying section (typically, the rectifying section included in the high-pressure part), heat can be transferred from the rectifying section to the stripping section.

A single heat exchange structure may be employed, or a plurality of heat exchange structures may be employed.

Here, discussion will be made on a configuration in which a low-pressure part includes the whole of the stripping section and a part of the rectifying section and a high-pressure part includes a part of the rectifying section. This configuration includes, for example, an embodiment in which a low-pressure column includes, above the stripping section, a part of the rectifying section and a high-pressure column includes the rest of the rectifying section. In such an embodiment, an overhead fluid of the low-pressure column (that is, a fluid discharged from the part of the rectifying section included in the low-pressure column) can be transferred to the column bottom of the high-pressure column via a compressor, and in this case, heat of the compressor outlet fluid can be given to a fluid present in the stripping section of the low-pressure column by heat exchange. For example, a heat exchange structure may be provided within the stripping section of the low-pressure column (for example, at a stage directly above the column bottom of the low-pressure column), and the overhead fluid of the low-pressure column may be supplied to the column bottom of the high-pressure column via the compressor and this heat exchange structure. By such heat exchange, heat can be transferred from the rectifying section included in the low-pressure column to the stripping section included in the low-pressure column. An example of such a structure is proposed in Japanese Patent Application No. 2012-080525.

The whole contents of Japanese Patent Application No. 2012-080525 and International Application PCT/JP2010/066498 (WO2011/043199) filed by the same applicant as the present Application are incorporated herein by reference.

[Examples of Preferable Configurations of HIDiC]

In a HIDiC using a double tube structure or plate fin type heat exchanger, it is difficult, for example, to obtain a side-cut product and to optimize a feedstock feed stage (feed stage). From this point of view, a distillation apparatus as described in WO2011/043199 is preferably used. Accordingly, the present invention can be suitably applied to a HIDiC having any of the following configurations.

1) A HIDiC including:
a high-pressure column including a trayed section or packed bed section used as a rectifying section;
a low-pressure column located higher than the high-pressure column and including a trayed section or packed bed section used as a stripping section;
a first pipe connecting a column top of the low-pressure column with a column bottom of the high-pressure column;
a compressor installed partway along the first pipe and configured to compress vapor from the column top of the low-pressure column and to transfer the compressed vapor to the column bottom of the high-pressure column;
a heat exchanger located at a predetermined stage of the high-pressure column (particularly, the rectifying section included in the high-pressure column);
a liquid withdrawal unit located at a predetermined stage of the low-pressure column (particularly, the stripping section included in the low-pressure column) and configured to withdraw a part of liquid from the predetermined stage to the outside of the low-pressure column;
a second pipe for introducing the liquid from the liquid withdrawal unit to the heat exchanger; and
a third pipe for introducing, to a stage directly below the liquid withdrawal unit, a fluid introduced through the second pipe to the heat exchanger and then discharged from the heat exchanger.

2) A HIDiC including:
a high-pressure column including a trayed section or packed bed section used as a rectifying section;
a low-pressure column located higher than the high-pressure column and including a trayed section or packed bed section used as a stripping section;
a first pipe for connecting a column top of the low-pressure column with a column bottom of the high-pressure column;
a compressor installed partway along the first pipe and configured to compress vapor from the column top of the low-pressure column and to feed the compressed vapor to the column bottom of the high-pressure column;
a liquid sump unit located at a predetermined stage of the low-pressure column (particularly, the stripping section included in the low-pressure column) and configured to hold liquid that has flowed downward;
a heat exchanger located in the liquid sump unit of the low-pressure column;
a partition plate that is set in a predetermined position of the high-pressure column (particularly, the rectifying section included in the high-pressure column) and that is configured for complete partition of upper and lower stages;
a second pipe for introducing vapor below the partition plate to the heat exchanger; and
a third pipe for introducing, to an upper side of the partition plate, a fluid introduced through the second pipe to the heat exchanger and then discharged from the heat exchanger.

3) The HIDiC according to 2), further including a pipe, which includes a control valve, for connecting spaces, that are located up and down and that sandwich the partition plate, with each other.

4) The HIDiC according to any one of 1) to 3), further including a feedstock supply pipe for supplying a feedstock to at least one of the column top of the low-pressure column and a predetermined stage of one of the trayed section and the packed bed section.

5) The HIDiC according to 4), further including a pump and a pipe for pressure-feeding a liquid stored in the column bottom of the high-pressure column to the feedstock supply pipe.

[Details of Configuration Example 1) of a HIDiC]

Figure 6:
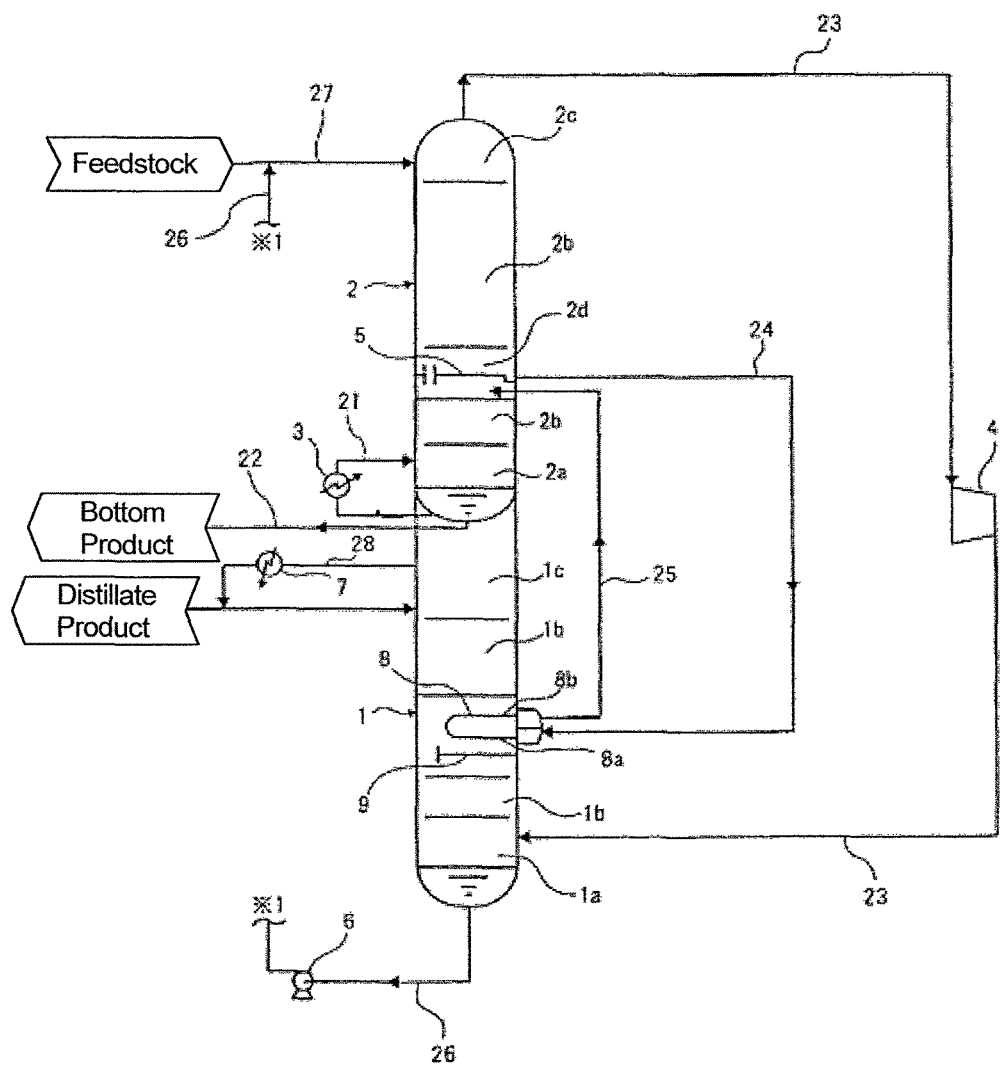
FIG. 6 shows an overall configuration of an example of a HIDiC.

FIG. 6 shows an overall configuration of a HIDiC having the configuration example 1) described above. This HIDiC includes a high-pressure column 1 and a low-pressure column 2 located higher than the high-pressure column 1. The high-pressure column 1 includes a column bottom 1a, a trayed section (or packed bed section) 1b and a column top 1c. The low-pressure column 2 also includes a column bottom 2a, a trayed section (or packed bed section) 2b and a column top 2c.

The trayed sections 1b and 2b are sections having several horizontal trays located therein. A space between adjacent trays is referred to as a stage. At each stage, gas-liquid contact is accelerated so as to cause mass transfer. As a result, a gas phase enriched in components that have higher volatility ascend to an upper stage, while a liquid phase enriched in components having lower volatility descends to a lower stage. Then, gas-liquid contact is performed again with a new liquid phase or gas phase so that mass transfer can be caused. Thus, there are more components with higher volatility at a higher stage of the column, there are more components with lower volatility at a lower stage, and a distillation operation is accomplished.

The packed bed section that can replace the trayed section is a section where a certain packing is installed in a hollow column, and gas-liquid contact is performed on its surface. By the same mechanism as that of the trayed section, there are more components with higher volatility at a higher part of the column, there are more components with lower volatility at a lower part, and a distillation operation is accomplished.

In FIG. 6, the trayed sections 1b and 2b (or packed bed sections) are shown as blank. In reality, however, the above-mentioned structures are employed.

Each of the high-pressure column 1 and the low-pressure column 2 will be described in detail. First, the low-pressure column 2 will be described.

A heater 3 referred to as a reboiler is disposed outside the column bottom 2a of the low-pressure column 2, and a pipe 21 is provided from a lower part of a space in the column bottom 2a through the heater 3 to an upper part of the space in the column bottom 2a. Accordingly a liquid descending through the trayed section 2b (or the packed bed section) of the low-pressure column 2 stays at the column bottom 2a. A part of this liquid is heated by the heater 3 to become vapor, and returns to the column bottom 2a. From the bottommost part of the column bottom 2a, a liquid bottom product that is rich in components with lower volatility is acquired through a pipe 22.

The column top 2c of the low-pressure column 2 is a position for supplying a feedstock. The column top 2c is connected via a compressor 4 to the column bottom 1a of the high-pressure column 1 by way of a pipe 23 (a line for directing an overhead vapor of a low-pressure part to a column bottom of a high-pressure part). Here, the feedstock feed position is at the column top 2c of the low-pressure column 2. However, the feedstock feed position may be at any stage of the trayed section 2b (or the packed bed section). In such a case, a part of the low-pressure column above the feedstock feed position corresponds to the rectifying section, a part of the low-pressure column below the feedstock feed position corresponds to the stripping section, and the inside of the high-pressure column corresponds to the rectifying section.

Furthermore, although there may be only one feedstock feed position, there may be a plurality of feedstocks (namely, there may be a plurality of feedstock feed positions at a plurality of different positions), and in this case, the feedstock feed positions may be, for example, at the column top 2c of the low-pressure column 2 and at another arbitrary stage (including a stage in the high-pressure column 1). With regard to the present invention, if there are a plurality of feedstock feed positions, any one amongst the plural feedstock feed positions may be selected to be regarded as a boundary, and a part above the selected feedstock feed position can be regarded as the rectifying section, and a part below the selected position can be regarded as the stripping section (here, the terms "above" and "below" are intended to mean above and below in terms of a distillation operation and do not always accord with the actual arrangement in the apparatus; even when the high-pressure column is located in a position lower than the low-pressure column, the inside of the high-pressure column is always "above" the inside of the low-pressure column).

Figure 7:
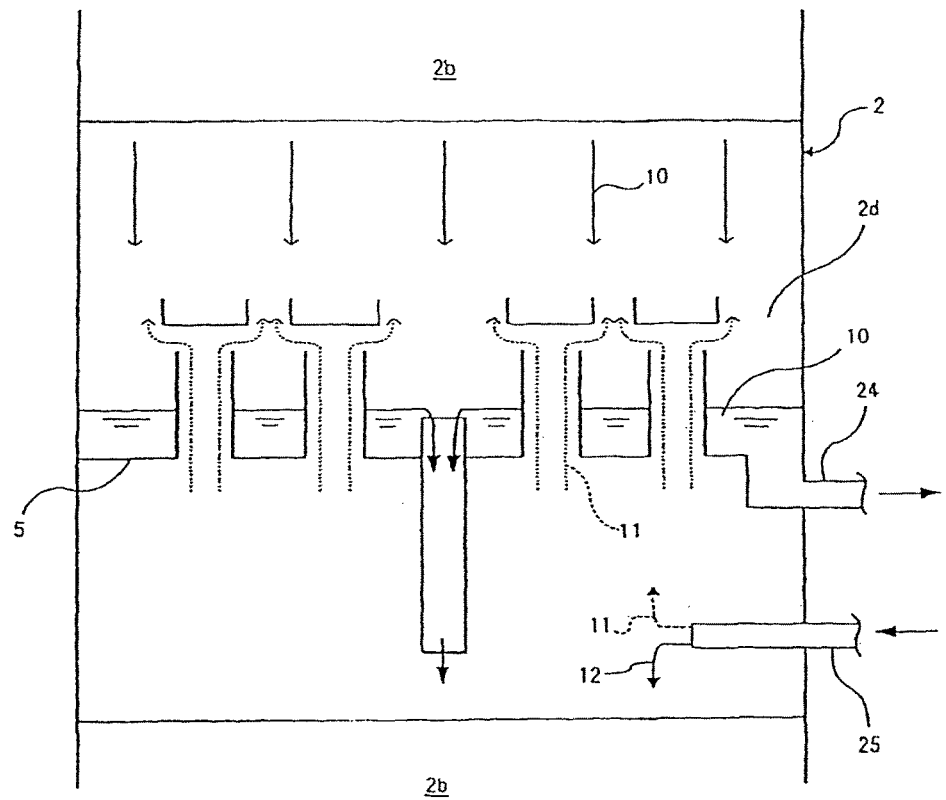
FIG. 7 shows a configuration of a liquid withdrawal unit shown in FIG. 6.

The trayed section 2b (or the packed bed section) of the low-pressure column 2 includes the liquid withdrawal unit 2d at a predetermined stage (particularly, at a stage within the stripping section). As shown in FIG. 7, the liquid withdrawal unit 2d holds a liquid 10, which has descended from an upper part of the low-pressure column 2, at a chimney tray for sump 5, and withdraws a part of the liquid 10 to the outside of the low-pressure column 2. A pipe 24 for directing a part of the liquid 10 to the high-pressure column 1 is connected to the liquid withdrawal unit 2d. A pipe 25 from the high-pressure column 1 is inserted through a shell wall of the low-pressure column 2 into a stage directly below the liquid withdrawal unit 2d. From the pipe 25 inserted into the stage directly below the liquid withdrawal unit 2d, a fluid which is a mixture of vapor 11 and liquid 12 is fed as described below, and the vapor 11 ascends while the liquid 12 descends.

Next, the high-pressure column 1 will be described.

One end of a pipe 26 is connected to a bottommost part of the column bottom 1a of the high-pressure column 1, while the other end of the pipe 26 is connected to a pipe 27 which supplies the feedstock to the column top 2c of the low-pressure column 2. In order to recycle the liquid staying at the column bottom 1a of the high-pressure column 1 to the column top 2c of the low-pressure column 2 located higher than the high-pressure column 1, a pump 6 is necessary partway along the pipe 26. The pipe 26 and a part of the pipe 27 (a downstream part from a meeting point with the pipe 26) together form a line for directing a column bottom liquid of a high-pressure part to a low-pressure part, particularly to the column top of the low-pressure part.

A condenser 7 is provided outside the column top 1c of the high-pressure column 1, and a pipe 28 is connected from an upper part of a space in the column top 1c to the condenser 7. Thus, vapor that has moved to the column top 1c of the high-pressure column 1 is cooled by the condenser 7 to become a liquid, and a distillate liquid that is rich in components with higher volatility is acquired. A part of this liquid is refluxed to the column top 1c as necessary.

In addition, a tube-bundle-type heat exchanger 8 is inserted into a predetermined stage (particularly, a stage within the rectifying section) of the trayed section 1b (or the packed bed section) of the high-pressure column 1. The parallel tube portions in the U-shaped tube of the tube-bundle-type heat exchanger 8 are placed along a chimney tray for sump 9 for temporarily holding a condensed liquid and for re-distributing vapor ascending from below. A lower tube portion 8a of the parallel tube portions is connected to the pipe 24 which is connected to the liquid withdrawal unit 2d of the low-pressure column 2. An upper tube portion 8b is connected to the pipe 25 that is inserted into the stage directly below the liquid withdrawal unit 2d.

An operation of the tube-bundle-type heat exchanger 8 will now be described.

Figure 8:
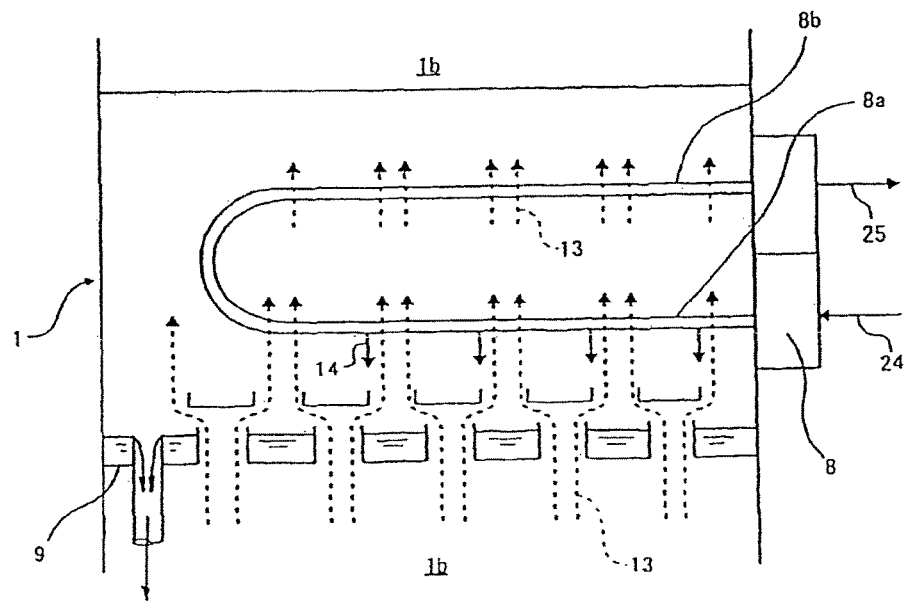
FIG. 8 shows a peripheral configuration of a tube-bundle-type heat exchanger located in a rectifying column shown in FIG. 6.

In the apparatus, the pressure and the temperature of vapor flowing out of the column top 2c of the low-pressure column 2 are raised by the compressor 4, and the resulting vapor is supplied to the column bottom 1a of the high-pressure column 1. The vapor 13 (refer to FIG. 8) thus raised in the temperature is introduced into and ascends through the trayed section 1b and comes into contact with the U-shaped tube of the tube-bundle-type heat exchanger 8. In this case, a liquid at an arbitrary stage (particularly, a stage within the stripping section) of the low-pressure column 2 is introduced through the pipe 24 to the lower tube portion 8a of the heat exchanger 8. Thus, the liquid in the tube portion 8a is heated by the heat of the vapor 13, and a part of the vapor 13 in contact with the tube portion 8a becomes a liquid 14, and this liquid descends. The upper tube portion 8b of the heat exchanger 8 is also heated by the heat of the vapor 13. Thus, the liquid introduced through the pipe 24 into the heat exchanger 8 changes into a fluid which is a mixture of a liquid phase and a gas phase while the liquid moves through the lower tube portion 8a and then through the upper tube portion 8b. This fluid then passes through the pipe 25 located outside the column to be introduced to the stage directly below the liquid withdrawal unit 2d of the low-pressure column 2 (refer to FIG. 6). Any pressure-feeding means such as a pump is not needed to circulate such fluids because the configuration described herein employs the thermo-siphon system.

In other words, because the liquid withdrawal unit 2d of the low-pressure column 2 is connected to the lower tube portion 8a of the heat exchanger 8 of the high-pressure column 1 via the pipe 24 and because the upper tube portion 8b of the heat exchanger 8 of the high-pressure column 1 is connected to the stage directly below the liquid withdrawal unit 2d of the low-pressure column 2 via the pipe 25, the liquid descends from the low-pressure column 2 to the high-pressure column 1 by gravity, which causes the above-mentioned fluid to flow from the high-pressure column 1 to the low-pressure column 2 even if no pump is provided.

As described above, in this example, heat can be removed from the vapor in the high-pressure column 1 by the heat exchanger 8, and the heat can be transferred from the high-pressure column 1 (particularly, the rectifying section) to the low-pressure column 2 (particularly, the stripping section) through the pipe 25. A heat transfer system using the pipes 24 and 25 and the heat exchanger 8 as in this example is configured as if a side condenser was installed at an arbitrary stage (particularly, a stage within the rectifying section) of the high-pressure column 1, and, simultaneously, as if a side reboiler was installed at an arbitrary stage (particularly, a stage within the stripping section) of the low-pressure column 2. Thus, as compared with a distillation apparatus that does not include such a heat transfer system, the amount of heat removed at the condenser 7 of the high-pressure column 1 can be reduced, and the amount of heat supplied at the reboiler 3 of the low-pressure column 2 can be reduced. As a result, a distillation apparatus having extremely high energy efficiency can be provided.

FIG. 6 shows only one heat transfer system. However, a plurality of heat transfer systems equivalent to, for example, 10 to 30% of the total number of theoretical stages can be installed. Needless to say, the number of heat transfer system(s) to be installed and the locations of the heat exchanger(s) and the pipes can be arbitrarily determined according to the design specification.

[Details of Configuration Example 2) of a HIDiC]

Next, a HIDiC having the above-mentioned configuration example 2) will be described. Components similar to those of the configuration example 1) will be described by using similar reference numerals.

Figure 9:
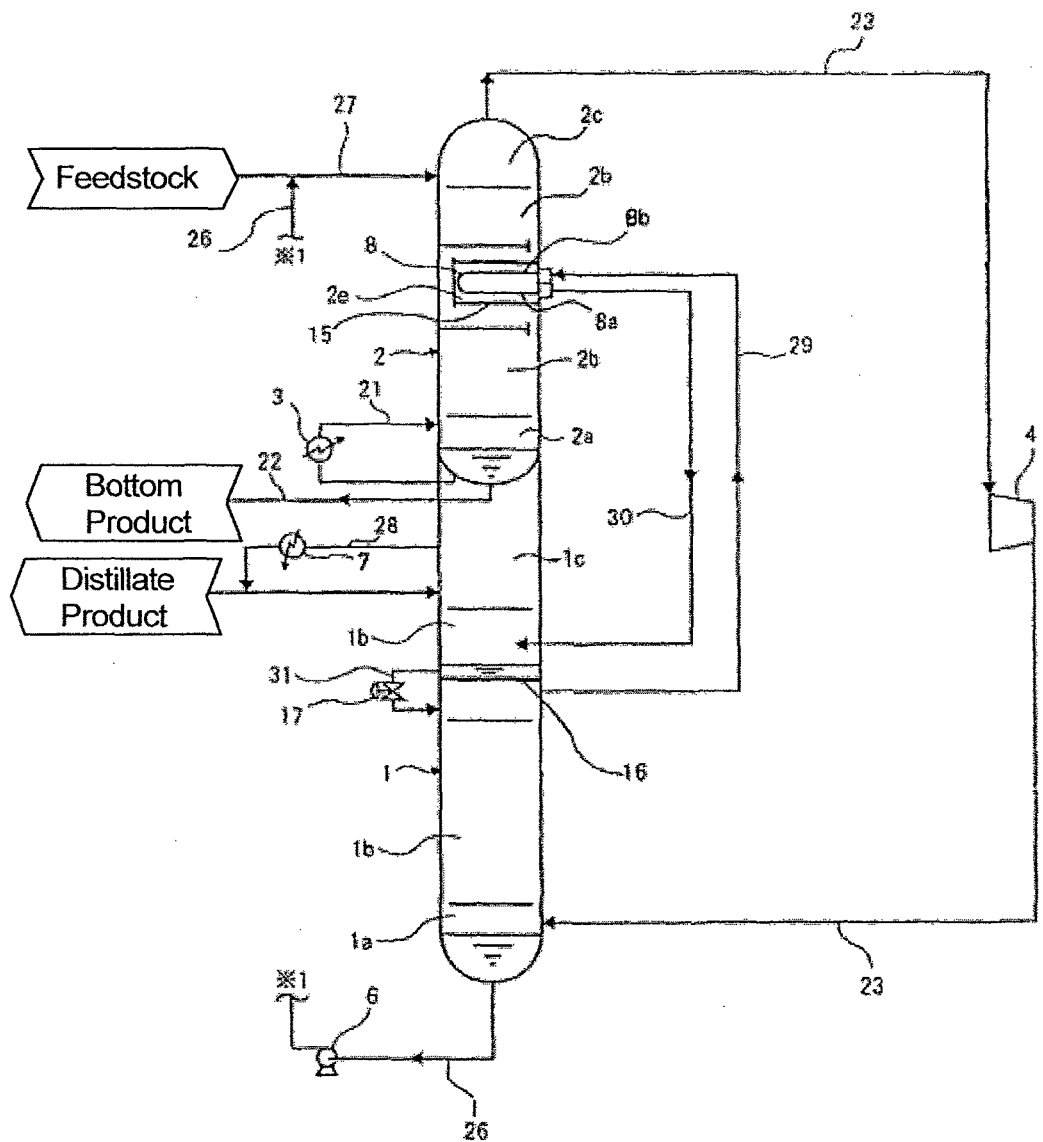
FIG. 9 shows an overall configuration of another example of a HIDiC.

FIG. 9 shows an overall configuration of a HIDiC having the configuration example 2). This distillation apparatus includes a high-pressure column 1 and a low-pressure column 2 located in a position higher than the high-pressure column 1. The high-pressure column 1 includes a column bottom 1a, a trayed section (or a packed bed section) 1b and a column top 1c. The low-pressure column 2 similarly includes a column bottom 2a, a trayed section (or a packed bed section) 2b and a column top 2c. The trayed section or the packed bed section has the same structure as described for the configuration example 1).

This example is different from the configuration example 1) in that a tube-bundle-type heat exchanger 8 is provided in the low-pressure column 2 (particularly, in the stripping section).

In the low-pressure column 2 of this example, components accompanying the column bottom 2a and the column top 2c (such as the reboiler 3, and the pipes 21, 22, 23 and 27) are the same as those used in the configuration example 1) as shown in FIG. 9, but components relating to the trayed section 2b (or the packed bed section) are different from those used in the configuration example 1).

Figure 10:
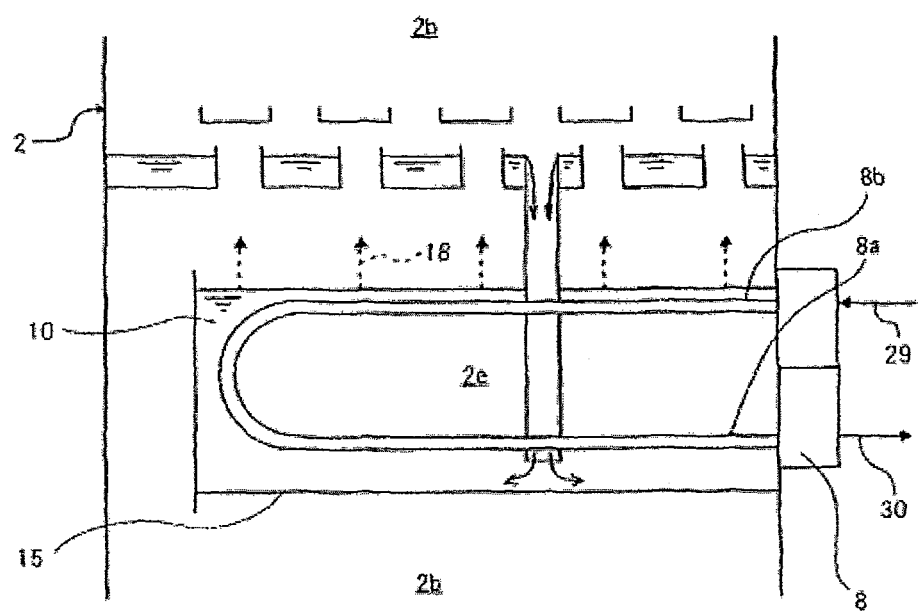
FIG. 10 shows a peripheral configuration of a tube-bundle-type heat exchanger located in a stripping column shown in FIG. 9.

The trayed section 2b (or the packed bed section) includes a liquid sump unit 2e at a predetermined stage (particularly, at a stage within the stripping section). The liquid sump unit 2e can store a predetermined amount of liquid 10 that has flowed down onto a chimney tray for sump 15, and can drop liquid spilled from the chimney tray for sump 15. A tube-bundle type heat exchanger 8 is inserted into the liquid sump unit 2e (refer to FIG. 10), so that a U-shaped tube of the tube-bundle-type heat exchanger 8 can be dipped in the liquid stored in the liquid sump unit 2e. Parallel tube portions 8a and 8b in the U-shaped tube of the tube-bundle-type heat exchanger 8 are placed along the chimney tray for sump 15.

A pipe 29 (refer to FIG. 9) for feeding a fluid from the high-pressure column 1 to the low-pressure column 2 is connected to the upper tube portion 8b of the parallel tube portions. A pipe 30 (refer to FIG. 9) for feeding a fluid from the low-pressure column 2 to the high-pressure column 1 is connected to the lower tube portion 8a.

An operation of the heat exchanger 8 in the liquid sump unit 2e will now described.

In this distillation apparatus, a feedstock liquid descends from the column top 2c of the low-pressure column 2 through a tray or a packed layer. This liquid 10 (refer to FIG. 10) stays at the liquid sump unit 2e on the chimney tray for sump 15 that is located at an arbitrary stage (particularly, at a stage within the stripping section). The U-shaped tube of the tube-bundle-type heat exchanger 8 is placed in the liquid sump unit 2e, and hence the U-shaped tube is dipped in the liquid 10. In this state, when high-temperature vapor present within the high-pressure column 1 is introduced through the pipe 29 into the upper tube portion 8b of the heat exchanger 8, a part of the liquid 10 in contact with the outer wall of the tube portions 8b and 8a, through which the high-temperature vapor moves, is heated to become vapor 18 and ascends (refer to FIG. 10). Furthermore, the high-temperature vapor having been introduced from the pipe 29 into the heat exchanger 8 changes into a fluid which is a mixture of a liquid phase and a gas phase, while the vapor moves through the upper tube portion 8b and then through the lower tube portion 8a. This fluid then passes through the pipe 30 located outside the low-pressure column to be introduced to a stage above a partition plate 16 of the high-pressure column 1 described later (refer to FIG. 9). A part above the partition plate 16 is set to have a lower operation pressure than a part below the partition plate 16, and the fluid is circulated by this pressure difference. For such fluid circulation, any pressure-feeding means such as a pump is not needed in this configuration as is the same as in the configuration example 1).

In other words, because the predetermined stage (particularly, the stage within the rectifying section) of the high-pressure column 1 is connected to the upper tube portion 8b of the heat exchanger 8 in the low-pressure column 2 via the pipe 29 and because the lower tube portion 8a of the heat exchanger 8 in the low-pressure column 2 is connected to the predetermined stage of the high-pressure column 1 via the pipe 30, high-pressure vapor present in the high-pressure column 1 ascends toward the heat exchanger 8 of the low-pressure column 2 through the pipe 29 owing to the pressure difference between the parts below and above the partition plate 16. As a result, the liquid condensed from the vapor within the heat exchanger 8 is then pushed out of the low-pressure column 2 to the pipe 30 located outside the low-pressure column, and then descends to the high-pressure column 1 by gravity. Thus, any pressure-feeding means such as a pump is not necessary.

Furthermore, the high-pressure column 1 of this example will be described.

Also with respect to the high-pressure column 1, components accompanying the column bottom 1a and the column top 1c (such as the condenser 7 and the pipes 23, 26 and 28) are the same as those used in the configuration example 1) as shown in FIG. 9, but components relating to the trayed section 1b (or the packed bed section) are different from those of the configuration example 1). Specifically, the trayed section 1b (or the packed bed section) of the high-pressure column 1 is completely partitioned into upper and lower stages by a partition plate 16 at a position (particularly, a position within the rectifying section) located partway along the trayed section 1b. The stage directly below the partition plate 16 communicates with a pipe 29. Ascending vapor in this stage is transferred, through the pipe 29 extending in the vertical direction, to the upper tube portion 8b of the heat exchanger 8 placed in the liquid sump unit 2e of the low-pressure column 2.

Into the upper stage of the partition plate 16, a pipe 30 from the low-pressure column 2 is inserted through the shell wall of the high-pressure column 1. A fluid which is a mixture of vapor and liquid is introduced into the upper stage of the partition plate 16 through this pipe 30, and the vapor ascends while the liquid descends to stay on the partition plate 16. The ascending vapor reaches the column top 1c, and then the vapor passes through the pipe 28 to be cooled by the condenser 7. As a result, a distillate liquid rich in components with high volatility is acquired.

Furthermore, the two stages vertically adjacent to each other with the partition plate 16 sandwiched therebetween can communicate with each other through a pipe 31 having a control valve 17. The liquid held on the partition plate 16 is fed to the stage below the partition plate 16 by an operation of opening the control valve 17 when appropriate.

As described above, in this example, heat can be removed from the high-pressure column 1 (particularly, from the rectifying section) to be transferred into the low-pressure column 2 (particularly, into the stripping section) by withdrawing vapor from the high-pressure column 1 (particularly, from the rectifying section) through the pipe 29 to the outside the column and introducing the vapor into the heat exchanger 8 in the low-pressure column 2 (particularly, in the stripping section). A heat transfer system using the pipes 29 and 30 and the heat exchanger 8, as in the case of this example, is configured as if a side condenser was installed at an arbitrary stage (particularly, a stage within the rectifying section) of the high-pressure column 1, and, simultaneously, as if a side reboiler was installed at an arbitrary stage (particularly, a stage within the stripping section) of the low-pressure column 2. Thus, as compared with a distillation apparatus that does not include such a heat transfer system, the amount of heat removed at the condenser 7 of the high-pressure column 1 can be reduced, and the amount of heat supplied at the reboiler 3 of the low-pressure column 2 can be reduced. As a result, a distillation apparatus having extremely high energy efficiency can be provided.

FIG. 9 shows only one heat transfer system. However, also in this example, the number of heat transfer system(s) to be installed and the locations of the heat exchanger(s) and the pipes can be arbitrarily determined according to the design specification as in configuration example 1).

EXAMPLES

The present invention will now be described in detail with reference to examples, but is not limited thereto.

Figure 3:
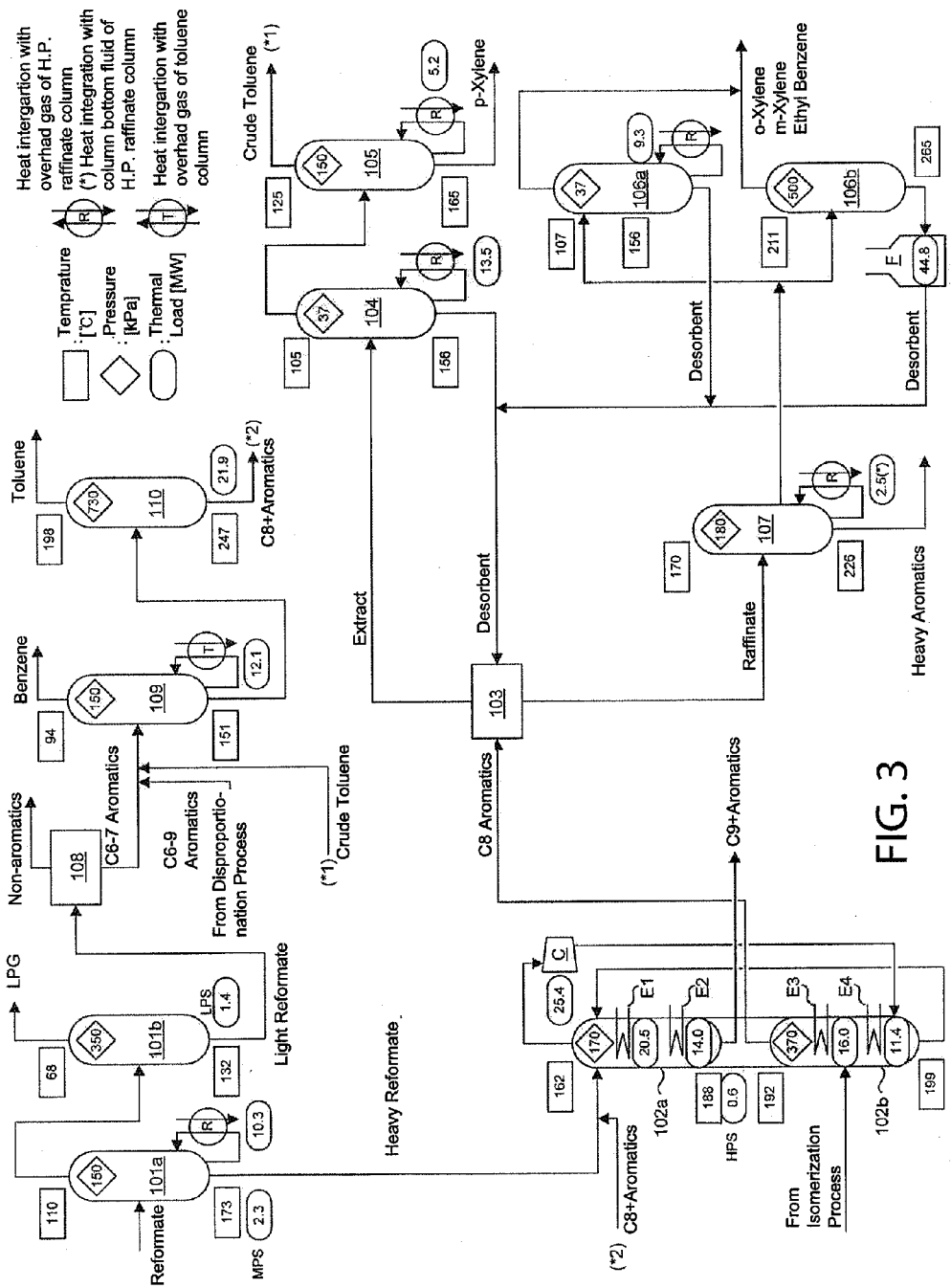
FIG. 3 is a schematic process flow diagram of Example 1.
Figure 4:
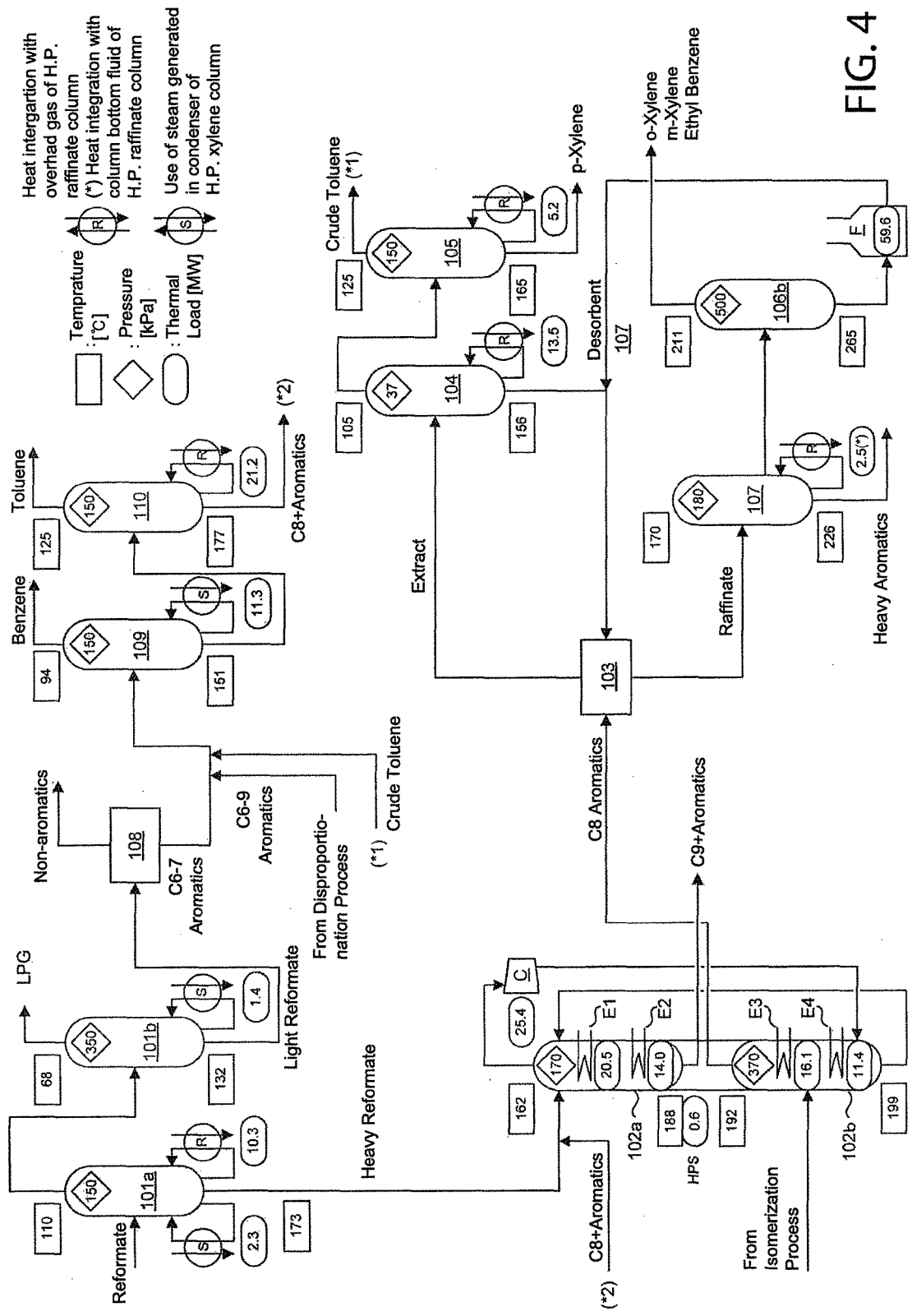
FIG. 4 is a schematic process flow diagram of Example 2.
Figure 5:
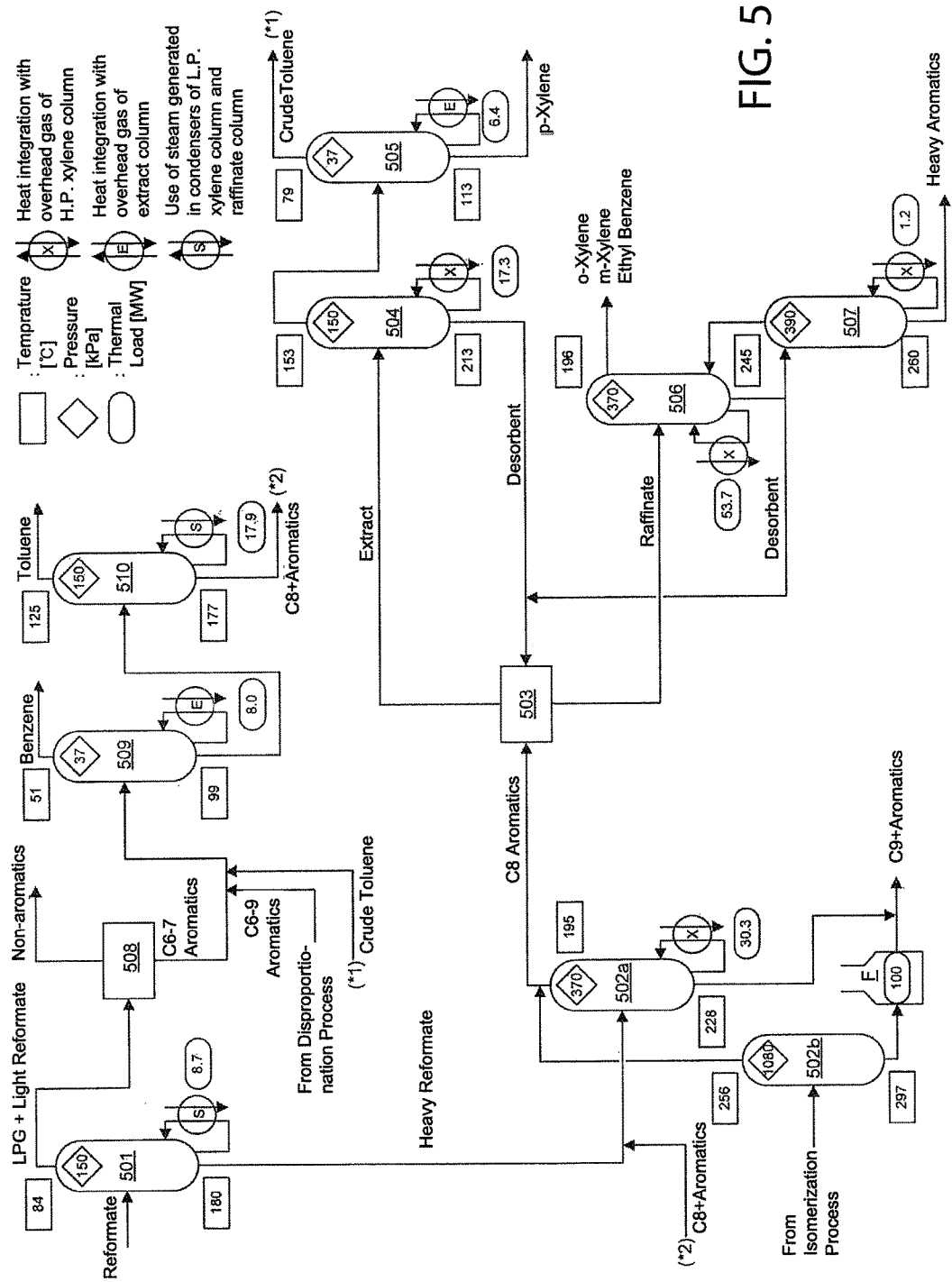
FIG. 5 is a schematic process flow diagram of Comparative Example.

With regard to each of apparatuses shown in FIGS. 3 to 5, the operation temperature (° C.) is shown in a corresponding rectangle, the operation pressure (kPaA) is shown in a corresponding square rotated by 45°, and the heat duty (MW) is shown in a corresponding ellipse. Here, the "heat duty" means the amount of exchanged heat (per unit time) if the heat exchange is conducted in a reboiler, or means the amount of heat of consumed fuel (per unit time) if heating is performed by a heating furnace. And with respect to a compressor, "heat duty" corresponds to a value of consumed power calculated in terms of primary energy (value in terms of primary energy=power÷0.366). Furthermore, each heat duty is shown as a relative value obtained by assuming that the heat duty of a heating furnace of a high-pressure xylene column 502b of FIG. 5 (Comparative Example) is 100.

Besides, in these drawings, a circle with which two lines (arrows) intersect represents a reboiler (a heat exchange structure). A letter such as R or T described inside the circle means that a fluid used as the heat source of the corresponding reboiler is as follows:

R: overhead vapor of a high-pressure raffinate column 106b (or, a column bottom fluid of the high-pressure raffinate column if a numerical value of the heat duty is followed by "(*)"), T: overhead vapor of a toluene column 110;

S: steam (in FIG. 4, steam with a saturation temperature of 185° C. generated by a condenser of a high-pressure xylene column 102b; in FIG. 5, steam with a saturation temperature of 185° C. generated by a low-pressure xylene column 502a and a raffinate column 506);

X: overhead vapor of a high-pressure xylene column 502b; and

E: overhead vapor of an extract column 504.

With respect to circles corresponding to heat exchange structures, only those involved in the multiple effect are shown in the drawings. Overhead condensers, heat exchangers used for preheating distillation columns, and the like are not shown.

Moreover, in these drawings, abbreviations "LPS", "MPS" and "HPS" stand for the following steams:

LPS: low-pressure steam (saturation temperature: 150° C.);

MPS: medium-pressure steam (saturation temperature: 185° C.); and

HPS: high-pressure steam (saturation temperature: 250° C.).

For example, a low-pressure reformate splitter 101a of FIG. 3 (Example 1) has a column top temperature of 110° C., a column bottom temperature of 173° C. and a pressure within the column of 150 kPaA. There are two kinds of heat duties for this splitter, that is, the amount of heat exchanged with overhead vapor of a high-pressure raffinate column 106b is 10.3 MW and the amount of heat exchanged with intermediate steam is 2.3 MW. Hence, heat in an amount of 12.6 MW in total is supplied to this low-pressure reformate splitter.

Example 1

FIG. 3 shows a process flow and operation conditions (temperatures, pressures and heat duties) employed in Example 1. A low-pressure reformate splitter 101a is operated at a pressure of 150 kPaA, uses overhead vapor of a high-pressure raffinate column 106b as a part of the heat source of its reboiler and uses medium-pressure steam as the rest of the heat source. A high-pressure reformate splitter 101b is operated at a pressure of 350 kPaA and uses low-pressure steam as the heat source of its reboiler.

As a xylene column, a HIDiC including a low-pressure xylene column 102a and a high-pressure xylene column 102b is applied. The low-pressure xylene column is operated at a pressure of 170 kPaA and uses high-pressure steam as the heat source of a reboiler provided therein. The high-pressure xylene column is operated at a pressure of 370 kPaA. For effecting internal heat exchange between the low-pressure xylene column (particularly, a stripping section included in the low-pressure xylene column) and the high-pressure xylene column (particularly, a rectifying section included in the high-pressure xylene column), four heat exchangers E1 to E4 are provided within the low-pressure or high-pressure reformate splitters.

An operation of the low-pressure xylene column 102a and the high-pressure xylene column 102b will now be described. A fraction separated by the low-pressure reformate splitter and enriched in an aromatic hydrocarbon component having 8 or more carbon atoms (that is, a heavy reformate) is supplied to the low-pressure xylene column 102a at a position located above the heat exchanger E1. Before being supplied to the low-pressure xylene column, the column bottom liquid of the low-pressure reformate splitter is mixed with a column bottom liquid (C8+ aromatics) of a toluene column 110. On the other hand, a fluid from an isomerization process is supplied to the high-pressure xylene column 102b at a position around a middle stage thereof.

From a position below the feed position of the column bottom liquid of the low-pressure reformate splitter (and below the heat exchanger E1 and above the heat exchanger E2), an internal liquid of the low-pressure xylene column is withdrawn (not shown; this position for withdrawing the fluid is referred to as the "withdrawal position to E3"). The withdrawn internal liquid is heated by the heat exchanger E3 (E3 is located above the feed position of the fluid supplied from the isomerization process), and the heated fluid is returned to a position below the withdrawal position to E3 and above the heat exchanger E2 (this position for returning the fluid is referred to as the "return position from E3"). The internal heat exchange structure described here is similar to the internal heat exchange structure shown in FIG. 6, and E3 corresponds to the heat exchanger 8 shown in FIG. 6.

Furthermore, separately from the aforementioned liquid withdrawal, an internal liquid of the low-pressure xylene column is withdrawn from a position below the return position from E3 and above the heat exchanger E2 (not shown; this position for withdrawing the fluid is referred to as the "withdrawal position to E4"). The thus withdrawn internal liquid is heated by the heat exchanger E4 (E4 is located below the feed position of the fluid supplied from the isomerization process in the high-pressure xylene column), and the heated fluid is returned to a position below the withdrawal position to E4. The internal heat exchange structure described here is also similar to the internal heat exchange structure shown in FIG. 6, and the heat exchanger E4 also corresponds to the heat exchanger 8 shown in FIG. 6.

From a position above the heat exchanger E3 located above the feed position of the fluid supplied from the isomerization process, overhead vapor of the high-pressure xylene column is withdrawn (not shown; this position for withdrawing the fluid is referred to as the "withdrawal position to E1"), and the withdrawn vapor is cooled by the heat exchanger E1 located above the withdrawal position to E3. The thus cooled internal fluid of the high-pressure xylene column is further cooled by a condenser (not shown) of the low-pressure xylene column to become a condensed liquid. A part of the condensed liquid is discharged from the HIDiC to be supplied to an adsorption column 103, and the rest of the condensed liquid is returned to the high-pressure xylene column at a position above the withdrawal position to E1. The heat exchange structure described here is similar to the internal heat exchange structure shown in FIG. 9, and the heat exchanger E1 corresponds to the heat exchanger 8 of FIG. 9.

A bottom liquid of the high-pressure xylene column is withdrawn from a position below the heat exchanger E4 and supplied to the column top of the low-pressure xylene column. The overhead vapor from the low-pressure xylene column is compressed by a compressor C (corresponding to the compressor 4 shown in FIG. 6 or 9), and then cooled by the heat exchanger E2 located in the column bottom of the low-pressure xylene column (however, the compressor C outlet fluid passing through the heat exchanger E2 is not shown). Thereafter, this fluid is supplied to the high-pressure xylene column at a position above a withdrawal position of the column bottom liquid and below the heat exchanger E4.

Internal heat exchange between the internal fluid of the low-pressure xylene column (particularly, the stripping section included in the low-pressure xylene column) and the internal fluid of the high-pressure xylene column (particularly, the rectifying section included in the high-pressure xylene column) is effected in four positions. In the low-pressure xylene column, the internal heat exchange is conducted in four positions below a stage where the column bottom fluid of the low-pressure reformate splitter is supplied. In the high-pressure xylene column, the internal heat exchange is conducted in one position above a stage where the fluid from the isomerization process is supplied, and in one position below this stage, as well as for the overhead vapor of the high-pressure xylene column and for a gas discharged from the compressor.

Specifically, the overhead vapor of the high-pressure xylene column passes through the heat exchanger E1 (which is located in the uppermost position amongst the four positions of the internal heat exchange in the low-pressure xylene column) to effect the heat exchange with the fluid present in the low-pressure xylene column. A part of the thus cooled overhead vapor is condensed, and the rest is all condensed by the heat exchanger (condenser) disposed downstream.

The internal liquid withdrawn from the withdrawal position to E3 (which corresponds to the second uppermost position amongst the four positions of the internal heat exchange in the low-pressure xylene column) passes through the heat exchanger E3 provided in the high-pressure xylene column, so as to effect the heat exchange with the fluid present in the high-pressure xylene column. The thus heated internal fluid is returned to a position below the withdrawal position to E3.

The internal liquid withdrawn from the withdrawal position to E4 (which corresponds to the third uppermost position out of the four positions of the internal heat exchange in the low-pressure xylene column) passes through the heat exchanger E4 provided in the high-pressure xylene column, so as to effect heat exchange with the fluid present in the high-pressure xylene column. The thus heated internal fluid is returned to a position below the withdrawal position to E4.

The overhead vapor of the low-pressure xylene column is compressed by the compressor, and then passes through the heat exchanger E2 (which is located in the lowermost position amongst the four positions of the internal heat exchange in the low-pressure xylene column), so as to effect the heat exchange with the fluid present in the low-pressure xylene column. The thus cooled vapor is supplied to the lowermost stage of the high-pressure xylene column.

As an overhead vapor of the HIDiC, the overhead vapor of the high-pressure xylene column 102b (that is, a fraction enriched in aromatic hydrocarbons having 8 carbon atoms) is supplied to the adsorption column 103 after condensation as described above. As a column bottom liquid of the HIDiC, a fraction enriched in aromatic hydrocarbons having 9 or more carbon atoms is discharged from the column bottom of the low-pressure xylene column 102a.

The fraction enriched in aromatic hydrocarbons having 8 carbon atoms separated by the HIDiC is then separated, by the adsorption column 103, into an extract, that is, a fraction enriched in para-xylene and a desorbent, and a raffinate, that is, a fraction enriched in xylene isomer(s) other than para-xylene and the desorbent. The separated extract is supplied to an extract column 104, and the separated raffinate is supplied to a low-pressure raffinate column and a high-pressure raffinate column.

The extract column 104 is operated at a pressure of 37 kPaA, and uses the overhead vapor of the high-pressure raffinate column as the heat source of its reboiler.

The low-pressure raffinate column is operated at a pressure of 37 kPaA, and uses the overhead vapor of the high-pressure raffinate column as the heat source of its reboiler. The high-pressure raffinate column is operated at a pressure of 500 kPaA, and includes a heating furnace F (with heat duty of 44.8 MW) as a reboiler.

The para-xylene purification column 105 is operated at a pressure of 150 kPaA, and uses the overhead vapor of the high-pressure raffinate column as a part of the heat source of its reboiler. As the rest of the heat source, a fluid from the column bottom of the high-pressure raffinate column is used (not shown). The heat duty of the reboiler is 7.5 MW in total as a sum of these two heat sources.

The pre-raffinate column 107 is operated at a pressure of 180 kPaA, and uses a fluid from the column bottom of the high-pressure raffinate column as the heat source of its reboiler.

The light reformate separated by the high-pressure reformate splitter 101b is supplied to an aromatics extraction apparatus 108, so as to be separated into aromatic hydrocarbons and non-aromatic hydrocarbons. The separated aromatic hydrocarbons are mixed with a stream from a disproportionation process and crude toluene separated by the para-xylene purification column 105, and then supplied to a benzene column 109.

The benzene column 109 is operated at a pressure of 150 kPaA, and uses the overhead vapor of the toluene column as the heat source of its reboiler.

The toluene column 110 is operated at a pressure of 730 kPaA, and uses hot oil (300° C.) as the heat source of its reboiler.

The heat and material balance of the aromatic hydrocarbon production apparatus described above was calculated, resulting in finding that the amount of necessary fuel can be reduced by approximately 50% as compared with that in Comparative Example described below. The total energy consumption, namely, a sum of the amount of necessary fuel, the amount of electricity consumed by the compressor used in the HIDiC and the amount of steam used in the aromatic hydrocarbon production apparatus, is reduced by approximately 4% as compared with that in Comparative Example.

Since the compressor is used in the xylene column in the present invention, the electric power is converted in terms of steam for comparison of the energy consumption.

In Example 1, the multiple effect is applied only to the distillation columns for xylene production process (namely, the reformate splitter, the extract column, the para-xylene purification column, the pre-raffinate column and the low-pressure raffinate column). Therefore, as compared with Example 2, Example 1 has advantages in operationability. Besides, because the low-pressure raffinate column is provided in Example 1, this example has an advantage in operationability due to the control of the distribution ratio described before.

Example 2

FIG. 4 shows a process flow and operation conditions (temperatures, pressures and heat duties) of Example 2. In this example, a process flow that can further reduce the total energy consumption as compared with that attained in Example 1 was constructed, by changing the heat sources of the reboilers of a benzene column and a toluene column. Specifically, the operation pressure of the toluene column was changed, and the overhead vapor of a high-pressure raffinate column was used as the heat source of the reboiler of the toluene column. Since the heat duty of the multiple effect increased, a distribution amount of the raffinate to the high-pressure raffinate column was increased for adjustment. As a result, it was found that the reduction of the total energy consumption attained by providing a low-pressure raffinate column was reduced. Therefore, from the viewpoint of the reduction of investment cost, the low-pressure raffinate column used in Example 1 is not provided, and the high-pressure raffinate column alone is provided as the raffinate column in Example 2. Furthermore, with regard to the toluene column, the operation pressure is changed, and the configuration of the multiple effect (the heat source of the reboiler) is changed. Besides, medium-pressure steam with a saturation temperature of 185° C. is generated by a condenser of the high-pressure xylene column 102b, and is used as the heat sources of the reboilers of the low-pressure reformate splitter, the high-pressure reformate splitter and the benzene column. Except for these changes, the same configuration as that of Example 1 is employed in this example. The heat and material balance was calculated for this example.

The low-pressure reformate splitter 101a is operated at a pressure of 150 kPaA, and uses the overhead vapor of the high-pressure raffinate column 106b as a part of the heat source of its reboiler and, as the rest of the heat source, uses the medium-pressure steam generated by the condenser of the high-pressure xylene column 102b. The high-pressure reformate splitter 101b is operated at a pressure of 350 kPaA, and uses the medium-pressure steam generated by the high-pressure xylene column 102b as the heat source of its reboiler.

The HIDiC is employed as a xylene column, and the low-pressure xylene column 102a is operated at a pressure of 170 kPaA and uses high-pressure steam as the heat source of the reboiler provided therein. The high-pressure xylene column 102b is operated at a pressure of 370 kPaA. For effecting internal heat exchange between the low-pressure xylene column and the high-pressure xylene column, the four heat exchangers are provided. The condenser provided for the high-pressure xylene column is used for generating the medium-pressure steam.

The extract column 104 is operated at a pressure of 37 kPaA and uses the overhead vapor of the raffinate column as the heat source of its reboiler.

The raffinate column 106b is operated at a pressure of 500 kPaA and equipped with a heating furnace F as the reboiler.

The para-xylene purification column 105 is operated at a pressure of 150 kPaA and uses the overhead vapor of the raffinate column as a part of the heat source of its reboiler. As the rest of the heat source, the fluid from the column bottom of the high-pressure raffinate column is used (not shown). The heat duty of the reboiler is 7.5 MW in total as a sum of these two heat sources.

The pre-raffinate column 107 is operated at a pressure of 180 kPaA and uses the fluid from the column bottom of the raffinate column as the heat source of its reboiler.

The benzene column 109 is operated at a pressure of 150 kPaA and uses the medium-pressure steam generated by the condenser of the high-pressure xylene column as the heat source of its reboiler.

The toluene column 110 is operated at a pressure of 150 kPaA and uses the overhead vapor of the raffinate column as the heat source of its reboiler.

The heat and material balance of the aromatic hydrocarbon production apparatus described above was calculated, resulting in finding that the amount of necessary fuel can be reduced by approximately 40% as compared with that in Comparative Example described below. The total energy consumption, that is, a sum of the amount of necessary fuel, the amount of electricity consumed by the compressor used in the HIDiC and the amount of steam used in the aromatic hydrocarbon production apparatus, is reduced by approximately 14% as compared with that in Comparative Example.

Since the compressor is used in the xylene column (the HIDiC) in the present invention, the amount of electricity is converted in terms of steam for comparison of the energy consumption.

In Example 2, the multiple effect is applied not only to the distillation columns for xylene production process (namely, the reformate splitter, the extract column, the para-xylene purification column and the pre-raffinate column) but also to the benzene column and the toluene column. Therefore, as compared with Example 1, Example 2 is advantageous in energy saving.

Comparative Example

As a comparative example, a process disclosed in US2012/0048711A1 is adopted.

In this comparative example, the heat and material balance was calculated for a process shown in FIG. 5. As shown in FIG. 5, a xylene column is not a HIDiC but includes two distillation columns arranged in parallel, namely, a low-pressure xylene column 502a and a high-pressure xylene column 502b. Furthermore, a reformate splitter 501 is configured with one distillation column, and hence, liquefied petroleum gas (LPG) components and a light reformate are not separated but supplied to an aromatics extraction process together. An aromatics extraction apparatus 508, a benzene column 509 and a toluene column 510 are the same as those of Example 1 (although their operation conditions and the configuration of the multiple effect are different). Furthermore, a raffinate column 506 is configured with one distillation column. A raffinate obtained from an adsorption column 503 is supplied to the raffinate column 506, a part of the column bottom liquid of the raffinate column is supplied to a pre-raffinate column 507, and the overhead vapor of the pre-raffinate column is returned to the raffinate column.

A heavy reformate obtained from the column bottom of the reformate splitter 501 and a stream from the aromatics extraction process (that is, the column bottom liquid of the toluene column 510) are distilled in the low-pressure xylene column 502a, and a stream from the isomerization process is distilled in the high-pressure xylene column 502b. A heating furnace F is provided as a reboiler of the high-pressure xylene column.

The overhead vapor of the high-pressure xylene column is used as the heat sources of the reboilers of the extract column 504 and the low-pressure xylene column 502a. Furthermore, the overhead vapor of the extract column is used as the heat sources of the reboilers of the benzene column 509 and the para-xylene purification column 505, and the overhead vapors of the low-pressure xylene column and the raffinate column are used for generating medium-pressure steam (saturation temperature: 185° C.).

The steam generated by using the overhead vapors of the low-pressure xylene column and the raffinate column is used as the heat sources of the reboilers of the reformate splitter and the toluene column 510. In this comparative example, since the steam generated by using the overhead vapors of the low-pressure xylene column and the raffinate column has a temperature at a comparatively low level, the steam is generated in an excessive amount beyond the amount used in the system, and hence the excessive steam is, for example, commercially sold.

The results (the heat duties) of Examples 1 and 2 and Comparative Example are together shown in Table 1. Each heat duty shown in Table 1, namely, the heat consumption in each aromatic hydrocarbon production apparatus, is relative energy consumption calculated by assuming that the amount of heat of fuel for the heating furnace F used as the heat source of the reboiler of the high-pressure xylene column 502b shown in the flow diagram of the comparative example is 100.

TABLE 1

| ENERGY CONSUMPTION (MW) | COMPARATIVE EXAMPLE | EXAMPLE 1 | EXAMPLE 2 |
|---|---|---|---|
| LOW-PRESSURE STEAM | | 1.4 | 0 |
| MEDIUM-PRESSURE STEAM | | 2.3 | 0 |
| HIGH-PRESSURE STEAM | | 0.6 | 0.6 |
| POWER (*) | | 25.4 | 25.4 |
| HOT OIL | | 21.9 | 0 |
| FUEL FOR HEATING FURNACE | | 44.8 | 59.6 |
| Total | 100 | 96.4 | 85.6 |
| ENERGY SAVING RATE (%) | 0 | 3.6 | 14.4 |

(*): converted in terms of primary energy

EXPLANATION OF LETTERS OR NUMERALS

1: high-pressure column (high-pressure part, high-pressure xylene column)
1a: column bottom
1b: trayed section (or packed bed section)
1c: column top
2: low-pressure column (low-pressure part, low-pressure xylene column)
2a: column bottom
2b: trayed section (or packed bed section)
2c: column top
2d: liquid withdrawal unit
2e: liquid sump unit
3: heater (reboiler)
4: compressor
5: tray
6: pressure-feeding means
7: condenser
8: tube-bundle-type heat exchanger
5, 15: chimney tray for sump
9: chimney tray for sump
10, 12, 14: liquid
11, 13, 18: vapor
16: partition plate
17: control valve
21, 22, 23, 24, 25, 26, 27, 28, 29, 30, 31: pipe
101a: low-pressure reformate splitter
101b: high-pressure reformate splitter 102: HIDiC (xylene column)
102a: low-pressure xylene column of HIDiC
102b: high-pressure xylene column of HIDiC
103: adsorption column
104: extract column
105: para-xylene purification column
106a: low-pressure raffinate column
106b: high-pressure raffinate column
107: pre-raffinate column
108: aromatics extraction apparatus
109: benzene column
110: toluene column
201: reformate splitter
202: xylene column
203: adsorption column
204: extract column
205: para-xylene purification column
206: raffinate column
207: pre-raffinate column
208: aromatics extraction apparatus
209: benzene column
210: toluene column
501: reformate splitter
502a: low-pressure xylene column
502b: high-pressure xylene column
503: adsorption column
504: extract column
505: para-xylene purification column
506: raffinate column
507: pre-raffinate column
508: aromatics extraction apparatus
509: benzene column
510: toluene column
C: compressor
E1 to E4: internal heat exchanger
F: heating furnace

What is claimed is:

1. An aromatic hydrocarbon production apparatus, comprising:
a first distillation apparatus configured to obtain, by distillation, from a feedstock, a fraction enriched in aromatic hydrocarbons having 8 or more carbon atoms and a fraction enriched in a component lighter than the aromatic hydrocarbons having 8 or more carbon atoms;
a second distillation apparatus configured to obtain, by distillation, from the fraction enriched in aromatic hydrocarbons having 8 or more carbon atoms obtained from the first distillation apparatus, a fraction enriched in aromatic hydrocarbons having 8 carbon atoms and a fraction enriched in an aromatic hydrocarbon having 9 or more carbon atoms;
an adsorption separation apparatus configured to separate para-xylene, by adsorption separation, from the fraction enriched in aromatic hydrocarbons having 8 carbon atoms obtained from the second distillation apparatus, and to obtain an extract and a raffinate, the extract being a stream containing a desorbent and para-xylene, and the raffinate being a stream containing the desorbent and a xylene isomer other than para-xylene;
a third distillation apparatus configured to obtain, by distillation, from the extract, a fraction enriched in para-xylene and a fraction enriched in the desorbent; and
a fourth distillation apparatus configured to obtain, by distillation, from the raffinate, a fraction enriched in the xylene isomer other than para-xylene and a fraction enriched in the desorbent,
wherein the second distillation apparatus is a heat integrated distillation column comprising:
a high-pressure part comprising the whole or a part of a rectifying section and configured to perform gas-liquid contact at a relatively high pressure;
a low-pressure part comprising the whole or a part of a stripping section and configured to perform gas-liquid contact at a relatively low pressure;
a line, comprising a pressurizing means, for directing an overhead vapor of the low-pressure part to a column bottom of the high-pressure part;
a line for directing a column bottom liquid of the high-pressure part to a column top of the low-pressure part; and
a heat exchange structure configured to transfer heat from the rectifying section to the stripping section, and
wherein the high-pressure part includes the whole of the rectifying section and the low-pressure part includes the whole of the stripping section; or
the low-pressure part includes the whole of the stripping section and also a part of the rectifying section, while the rest of the rectifying section is included in the high-pressure part; or
the high-pressure part includes the whole of the rectifying section and also a part of the stripping section, while the rest of the stripping section is included in the low-pressure part.

2. The apparatus according to claim 1, wherein
the first distillation apparatus comprises a low-pressure distillation column configured to be operated at a relatively low pressure and a high-pressure distillation column configured to be operated at a relatively high pressure, which are arranged in series,
the low-pressure distillation column of the first distillation apparatus is a distillation column configured to obtain, from the feedstock, the fraction enriched in aromatic hydrocarbons having 8 or more carbon atoms and the fraction enriched in a component lighter than the aromatic hydrocarbons having 8 or more carbon atoms, and
the high-pressure distillation column of the first distillation apparatus is a distillation column configured to obtain, from the fraction enriched in a component lighter than the aromatic hydrocarbons having 8 or more carbon atoms obtained from the low-pressure distillation column of the first distillation apparatus, a fraction enriched in a hydrocarbon having from 6 to 7 carbon atoms and a fraction enriched in a component lighter than the hydrocarbon having from 6 to 7 carbon atoms.

3. The apparatus according to claim 2, wherein the aromatic hydrocarbon production apparatus is configured to use an overhead vapor of the fourth distillation apparatus as a heat source of one or more reboilers selected from the group consisting of a reboiler provided for the low-pressure distillation column of the first distillation apparatus and a reboiler provided for the third distillation apparatus.

4. The apparatus according to claim 3, further comprising a fifth distillation apparatus configured to purify, by distillation, para-xylene contained in the fraction enriched in para-xylene obtained from the third distillation apparatus, wherein
the aromatic hydrocarbon production apparatus is configured to use the overhead vapor of the fourth distillation apparatus as a heat source of a reboiler provided for the fifth distillation apparatus.

5. The apparatus according to claim 3, wherein
the fourth distillation apparatus comprises a low-pressure distillation column configured to be operated at a relatively low pressure and a high-pressure distillation column configured to be operated at a relatively high pressure, which are arranged in parallel,
the low-pressure distillation column of the fourth distillation apparatus is a distillation column configured to obtain, from a part of the raffinate, a fraction enriched in the xylene isomer other than para-xylene and a fraction enriched in the desorbent,
the high-pressure distillation column of the fourth distillation apparatus is a distillation column configured to obtain, from another part of the raffinate, a fraction enriched in the xylene isomer other than para-xylene and a fraction enriched in the desorbent, and
the overhead vapor of the fourth distillation apparatus is an overhead vapor of the high-pressure distillation column of the fourth distillation apparatus.

6. The apparatus according to claim 5, wherein the aromatic hydrocarbon production apparatus is configured to use the overhead vapor of the high-pressure distillation column of the fourth distillation apparatus as a heat source of a reboiler provided for the low-pressure distillation column of the fourth distillation apparatus.

7. The apparatus according to claim 3, further comprising:
an aromatics extraction apparatus configured to obtain, by solvent extraction, from the fraction enriched in a hydrocarbon having from 6 to 7 carbon atoms obtained from the high-pressure distillation column of the first distillation apparatus, a stream enriched in an aromatic hydrocarbon having from 6 to 7 carbon atoms and a stream enriched in a non-aromatic hydrocarbon having from 6 to 7 carbon atoms;
a sixth distillation apparatus configured to obtain, by distillation, from the stream enriched in an aromatic hydrocarbon having from 6 to 7 carbon atoms obtained from the aromatics extraction apparatus, a fraction enriched in benzene and a fraction enriched in a component heavier than benzene; and
a seventh distillation apparatus configured to obtain, by distillation, from the fraction enriched in a component heavier than benzene obtained from the sixth distillation apparatus, a fraction enriched in toluene and a fraction enriched in a component heavier than toluene,
wherein the aromatic hydrocarbon production apparatus is configured to use the overhead vapor of the fourth distillation apparatus as a heat source of a reboiler provided for the seventh distillation apparatus.

8. The apparatus according to claim 7, wherein the fourth distillation apparatus consists of a single distillation column, and the overhead vapor of the fourth distillation apparatus is an overhead vapor of this single distillation column.

9. The apparatus according to claim 1, wherein an eighth distillation apparatus configured to remove, by distillation, an impurity contained in the raffinate is disposed between the adsorption separation apparatus and the fourth distillation apparatus.

10. The apparatus according to claim 2, wherein an eighth distillation apparatus configured to remove, by distillation, an impurity contained in the raffinate is disposed between the adsorption separation apparatus and the fourth distillation apparatus.

11. The apparatus according to claim 3, wherein an eighth distillation apparatus configured to remove, by distillation, an impurity contained in the raffinate is disposed between the adsorption separation apparatus and the fourth distillation apparatus.

12. The apparatus according to claim 5, wherein the high-pressure distillation column of the fourth distillation apparatus comprises a reboiler equipped with a heating furnace.

* * * * *